United States Patent [19]

Yanagisawa

[11] Patent Number: 5,736,376

[45] Date of Patent: Apr. 7, 1998

[54] RECOMBINANT ENDOTHELIN CONVERTING ENZYME-2 AND ITS USE IN ECE INHIBITOR SCREENING

[75] Inventor: Masashi Yanagisawa, Dallas, Tex.

[73] Assignee: Board of Regents, The University of Texas System, Austin, Tex.

[21] Appl. No.: 574,763

[22] Filed: Dec. 19, 1995

[51] Int. Cl.[6] .............................. C12N 9/48; C12P 21/06; C12P 19/34; C07H 21/04

[52] U.S. Cl. ...................... 435/212; 435/69.1; 435/70.1; 435/70.3; 435/91.2; 435/814; 536/23.2

[58] Field of Search .......................... 435/69.1, 70.1, 435/70.3, 91.2, 212, 814; 536/23.2

[56] References Cited

U.S. PATENT DOCUMENTS

| | | | |
|---|---|---|---|
| 5,231,166 | 7/1993 | Masaki et al. | 530/324 |
| 5,294,569 | 3/1994 | Masaki et al. | 536/23.5 |
| 5,338,726 | 8/1994 | Shiosaki et al. | 514/17 |
| 5,384,243 | 1/1995 | Gutkind et al. | 435/6 |
| 5,427,922 | 6/1995 | Fujisawa et al. | 435/69.1 |

OTHER PUBLICATIONS

Ahn et al., "The Endothelin-Converting Enzyme from Human Umbilical Vein is a Membrane-Bound Metalloprotease Similar to that from Bovine Aortic Endothelial Cells", *Proc. Natl. Acad. Sci. USA*, 89:8606–8610, 1992.

Anderson and Orci, "A View of Acidic Intracellular Compartments", *The Journal of Cell Biology*, 106:539–543, 1988.

Arai et al., "Aspergillomarasmine A and B, Potent Microbial Inhibitors of Endothelin-Converting Enzyme", *Biosci. Biotech. Biochem.*, 57(11):1944–1945, 1993.

Arai et al., "Cloning and Expression of a cDNA Encoding an Endothelin Receptor", *Nature*, 348:730–732, 1990.

Bax and Saxena, "The Current Endothelin Receptor Classification: Time for Reconsideration?", *Elsevier Science LTD—TiPS*, 15:379–386, 1994.

Baynash et al., "Interaction of Endothelin-3 with Endothelin-B Receptor Is Essential for Development of Epidermal Melanocytes and enteric Neurons", *Cell*, 79:1277–1285, 1994.

Clozel et al., "Pathophysiological Role of Endothelin Revealed by the First Orally Active Endothelin Receptor Antagonist", *Nature*, 365:759–761, 1993.

Douglas et al., "Novel Receptor Antagonists Welcome a New Era in Endothelin Biology", *Elsevier Science Ltd—TiPS*, 15:313–316, 1994.

Emoto and Yanagisawa, "Endothelin-Converting Enzyme-2 Is a Membrane-Bound, Phosphoramidon-Sensitive Metalloprotease with Acidic pH Optimum", *The Journal of Biological Chemistry*, 270(25):15262–15268, 1995.

Giaid et al., "Expression of Endothelin-1 in the Lungs of Patients with Pulmonary Hypertension", *The New England Journal of Medicine*, 328(24):1732–1739, 1993.

Hosada et al., "Targeted and Natural (Peibald-Lethal) Mutations of Endothelin B Receptor Gene Produce Megacolon Associated with Spotted Coat Color in Mice", *Cell*, 79:1267–1276, 1994.

Inoue et al., "The Human Endothelin Family: Three Structurally and Pharmacologically Distinct Isopeptides Predicted by Three Separate Genes", *Proc. Natl. Acad. Sci. USA*, 86:2863–2867, 1989.

Inoue et al., "The Human Preproendothelin-1 Gene", *The Journal of Biological Chemistry*, 264(25):14954–14959, 1989.

Kurihara et al., "Elevated Blood Pressure and Craniofacial Abnormalities in Mice Deficient in Endothelin-1", *Nature*, 368(21):703–710, 1994.

Lee et al., "Molecular Cloning and Primary Structure of Kell Blood Group Protein", *Proc. Natl. Acad. Sci. USA*, 88:6353–6357, 1991.

Matsumoto et al., "Abundance of Endothelin-3 in Rat Intestine, Pituitary Gland and Brain", *Biochemical and Biophysical Research Communications*, 164(1):74–80, 1989.

McMahon et al., "Phosphoramidon Blocks the Pressor Activity of Porcine Big Endothelin-1-(-139) in vivo and Conversion of Big Endothelin-1-(1-39) to Endothelin-1-(1-21) in vitro", *Proc. Natl. Acad. Sci. USA*, 88:703–707, 1991.

Nishikori et al., "Receptor Binding Affinity and Biological Activity of C-Terminal Elongated Forms of Endothelin-1", *Neurochem.Int.*, 18(4):535–539, 1991.

Ohlstein et al., "SB 209670, A Rationally Designed Potent Nonpeptide Endothelin Receptor Antagonist", *Proc. Natl. Acad. Sci. USA*, 91:8052–8056, 1994.

Ohnaka et al., "Purification and Characterization of a Phosphoramidon-sensitive Endothelin-converting Enzyme inPorcine Aortic Endothelium," *The Journal of Biological Chemistry*, 268(35):26759–26766, 1993.

Okada et al., "Conversion of Big Endothelin-1 By Membrane-Bound Metalloendopeptidase in Cultured Bovine Endothelial Cells," *Biochemical and Biophysical Research Communications*, 171(3):1192–1198.

Okada, et al., "Big Endothelin-1 Structure Important for Specific Processing by Endothelin-Converting Enzyme of Bovine Endothelian Cells", *Eur. J. Biochem.*, 218:493–498, 1993.

(List continued on next page.)

*Primary Examiner*—Robert A. Wax
*Assistant Examiner*—Elizabeth Slobodyansky
*Attorney, Agent, or Firm*—Arnold, White & Durkee

[57] ABSTRACT

Disclosed is a nucleic acid segment encoding endothelin converting enzyme-2 (ECE-2), that produces mature ET-1 from big ET-1 both in vitro and in transfected cells. Also disclosed is a polypeptide composition comprising partially purified ECE-2 and methods of using ECE-2 to screen candidate substances as inhibitors of ECE-2. Methods of producing recombinant ECE-2 are also disclosed.

7 Claims, 5 Drawing Sheets

OTHER PUBLICATIONS

Opgenorth et al., "Endothelin–Converting Enzymes", *The FASEB Journal*, 6:2653–2659, 1992.

Rawlings and Barrett, "Evollutionary Families of Peptidases", *Biochem J.*, 290:205–218, 1993.

Sakamoto et al., "Distinct Subdomains of Human Endothelin Receptors Determine Their Seklectivity to Endothelin$_A$–Selective Antagonist and Endothelin$_b$–Selective Agonists", *The Journal of Biological Chemistry*, 268(12);8547–8553, 1993.

Sakurai et al., "Cloning of cDNA Encoding a Non–Isopeptide–Selective Subtype of the Endothelin Receptor", *Nature*, 348:732–735, 1990.

Sawamura et al., "Phosphoramidon Inhibits the Intravellular Conversion of Big Endothelin–1 to Endothelin–1 in Cultured Endothelial Cells", *Biochemical and Biophysical Research Communications*, 174(2):779–784, 1991.

Seidah et al., "Mammalian Paired Basic Amino Acid Convertases of Prohormones and Proproteins$^a$", *Annals of the New York Academy of Sciences*, 680:135–146, 1993.

Shimada et al., "Cloning and Functional Expression of Endothelin–Converting Enzyme from Rat Endothelial Cells", *The Journal of Biological Chemistry*, 269(28):18275–18278, 1994.

Suzuki et al., "A Sensitive Sandwich–Enzyme Immunoassay for Human Endothelin", *Journal of Immunological Methods*, 118:245–250, 1989.

Takahashi et al., "Purification and Characterization of Endothelin–Converting Enzyme from Rat Lung", *The Journal of Biological Chemistry*, 268(28):21394–21398, 1993.

Turner, Anthony J., "Endothelin–converting Enzymes and Other Families of Metallo–endopeptidases", *Biochemical Society Transactions*, 21:697–701, 1993.

Vijayaraghavan et al., "The Hydrolysis of Endothelins by Neutral Endopeptidase 24.11 (Enkephalinase)," *The Journal of Biological Chemistry*, 265:(24)14150–14155.

Waxman et al., "Identification and Characterization of Endothelin Converting Activity from EAHY 926 Cells: Evidence for the Physiologically Relevant Human Enzyme," *Archives of Biochemistry and Biophysics*, 308(1):240–253, 1994.

Wilhelm et al., "Matrix Metalloproteinase–3 (Stromelysin–1)", *The Journal of Biological Chemistry*, 268(29):21906–21913, 1993.

Xu et al., "ECE: A Membrane–Bound Metalloprotease That Catalyzes the Proteolytic Activation of Big Endothelin–1", *Cell*, 78:473–485, 1994.

Yanagisawa et al., "A Novel Potent Vasoconstrictor Peptide Produced by Vascular Endothelial Cells", *Nature*, 332:411–415, 1988.

Yanagisawa, Masashi, "The Endothelin System: A New Target for Therapeutic Intervention", *Editorial Circulation*, 89(3):1320–1323, 1994.

Malfroy et al., "Molecular Cloning and Amino Acid Sequence of Human Enkephalinase (Neutral Endopeptidase", 229(1):206–210, 1988.

RECOMBINANT ENDOTHELIN CONVERTING ENZYME-2 AND ITS USE IN ECE INHIBITOR SCREENING

BACKGROUND OF THE INVENTION

1. Field of the Invention

The present invention relates generally to the field of vascular homeostasis, the control of vasodilation by peptide regulators and their role in diseases such as high blood pressure, kidney disease and certain types of strokes. More particularly, the invention relates to the field of proteases that activate the peptide regulators and to the family of membrane bound metalloproteases.

2. Description of the Related Art

Endothelins are a family of 21-amino-acid peptides that possess a wide variety of biological activities (Yanagisawa, 1994; Rubanyi and Polokoff, 1994). The first member of this family, endothelin-1 (ET-1), was identified as an endothelium-derived vasoconstrictor (Yanagisawa et al., 1988). Three known members of the mammalian endothelin family, ET-1, ET-2 and ET-3, are produced in various tissues (Inoue et al., 1989). They act on two distinct subtypes of G-protein coupled receptors termed $ET_A$ and $ET_B$, which are expressed on a variety of target cells (Arai et al., 1990; Sakurai et al., 1990; Bax and Saxena, 1994). Recent studies with specific endothelin receptor antagonists have indicated that endothelins play important roles in a number of animal models for vascular diseases, and possibly in certain pathological conditions in humans (Ohlstein et al., 1994; Clozel et al., 1993; Giaid et al., 1993; Douglas et al., 1994). Mice carrying targeted mutations in the ET-1, ET-3 and $ET_B$ receptor genes exhibit developmental abnormalities that suggest a role for endothelins in the development of neural crest-derived tissues (Kurihara et al., 1994; Baynash et al., 1994; Hosoda et at., 1994).

Endothelins are produced from ≈200 residue prepropolypeptides, which are first processed by the subtilisin family of prohormone processing enzyme(s) (Seidah et al., 1993) into biologically inactive, 38–41 residue intermediates called big ET-1, 2 and 3. The C-terminal halves of big endothelins are then clipped off between Trp21 and Val/Ile22, yielding the N-terminal, 21-residue active endothelins. This proteolytic conversion is catalyzed by specific protease(s) called endothelin converting enzyme(s) (ECE) (Yanagisawa et al., 1988). Several lines of evidence suggest that the physiologically relevant ECE(s) are sensitive to the metalloprotease inhibitor phosphoramidon (Opgenorth et al., 1992). Thus, in whole animal preparations and isolated perfused tissues, the vasopressor actions of exogenously administered big endothelins are inhibited by phosphoramidon. The processing of endogenous big ET-1 in cultured endothelial cells is also inhibited by phosphoramidon. Biochemical studies have shown that the ECE from endothelial cells and other sources is a membrane-bound metalloprotease (Ahn et al., 1992; Okada et al., 1993; Takahashi et al., 1993). One such metalloprotease, ECE-1, was recently cloned (Shimada et al., 1994; Xu et al., 1994). ECE-1 was shown to be a type II membrane-bound metalloprotease that processed endogenously produced big ET-1 intracellularly and exogenously supplied big ET-1 on the cell surface (Xu et al., 1994). Unfortunately, it has been difficult to relate these ECE activities assayed in the test tube to the physiologically relevant ECE activities that function in vivo. In addition it has not been possible to overproduce ECE in order to determine the molecular mechanisms of vasoconstriction and to control vasoconstriction in animals in pathological situations.

SUMMARY OF THE INVENTION

The present invention seeks to overcome these and other drawbacks inherent in the prior art by providing an isolated ECE-2, a novel membrane-bound metalloprotease, and isolated nucleic acid segments encoding ECE-2. With the use of the present invention, high levels of ECE-2 activity can be expressed in transfected tissue culture cells or in prokaryotic cells. In addition, cell lines which permanently express high levels of ECE-2 can be readily generated and used. This use of the present invention will allow the identification of naturally occurring but unknown vasoconstriction inhibitors as well as the design of novel antagonists or inhibitors of endothelin mediated vasoconstriction. Such inhibitors or antagonists will be useful in the treatment of various disorders associated with the release of endothelins such as acute myocardial infarction, acute renal failure and posthemorrhagic cerebral vasospasm.

In certain embodiments the present invention is an isolated nucleic acid segment that encodes an endothelin converting enzyme-2 (ECE-2) polypeptide and preferably that encodes an amino acid sequence according to SEQ ID NO:2, or an isolated nucleic acid segment that is hybridizable to the sequence designated herein as SEQ ID NO:1 under conditions that include 0.1X SSC/0.1% SDS at 60° C. The nucleic acid segment of the present invention may also be defined as comprising a nucleic acid sequence consisting of the nucleic acid sequence designated herein as SEQ ID NO:1. It is understood that in addition to the nucleic acid sequences disclosed herein, the complement of the disclosed sequences, the RNA sequences encoded by the DNA segments and the complement of the RNA sequences are also encompassed by the present claimed invention.

The complement of a DNA or RNA sequence is well known in the art and is based on the Watson-Crick pairing of nucleic acid polymers. The complement of a nucleic acid segment is generated by converting all "G" residues to "C" residues, all "C" residues to "G" residues, all "A" residues to "T" (in the case of DNA) or "U" (in the case of RNA) and all "T" or "U" residues to "A", and then reversing the 5' to 3' orientation of the generated sequence. As used herein therefore, the term "complement" defines a second strand of nucleic acid which will hybridize to a first strand of nucleic acid to form a duplex molecule in which all base pairs are matched as G:C, C:G, A:T/U or T/U:A.

The present invention may also be described in certain embodiments as a nucleic acid segment that is hybridizable to the nucleic acid segment of SEQ ID NO:1 under high stringency conditions. Hybridizable is understood to mean the formation of a double stranded molecule or a molecule with partial double stranded structure. High stringency conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. Some examples of ranges that may be employed are for low stringency, from 0.15–0.9M NaCl at a temperature of 20°–50° C. might be employed, and for high stringency, from 0.02–0.15M NaCl at a temperature of 50°–70° C. might be employed. It is understood that the temperature and ionic strength of a desired stringency ate applicable to particular probe lengths, to the length and base content of the sequences and to the presence of formamide or other solvents in the hybridization mixture, and that these ranges are mentioned by way of example only.

It is understood in the art that a nucleic acid sequence will hybridize with a complementary nucleic acid sequence under high stringency conditions even though some mismatches may be present. Such closely matched, but not perfectly complementary sequences are also encompassed by the present invention. For example, differences may occur through genetic code degeneracy, or by naturally occurring or man made mutations, or extraneous sequence may be present flanking the hybridization target sequence, and such mismatched sequences would be encompassed by the present claimed invention. For example, methods now exist in the art to substitute any amino acid at any position along an amino acid sequence. In light of the present discovery, one could choose particular amino acids to change, or even to delete in order to change various aspects of the ECE-2 protein, such as solubility, substrate binding, etc. Once a gene and amino acid sequence are discovered, as in the present disclosure, such manipulations are routine in the art and all such altered protein or amino acid sequences that are derived from the present discovery would be encompassed by the present claims.

A nucleic acid segment of the present invention may also be under the control of a promoter, or in other words, operatively linked to a promoter. The promoter may be the promoter which normally controls the expression of the DNA segment in its native tissue, or it may be a heterologous promoter. By heterologous promoter is meant a promoter that is derived from another source, either another location in the genome within the same cell or from a different type of cell or even from a different organism. The promoter sequence is then joined to the nucleic acid segment in an upstream position (5') from the start of the gene. Preferred promoters include, but are not limited to, cytomegalovirus major immediate early gene promoter, simian virus 40 late gene promoter and Baculovirus *Autographa californica* nuclear polyhedrosis virus polyhedrin gene promoter. Alternatively, the promoter may be an inducible promoter such as the lactose operon promoter.

The nucleic acid segment of the present invention may also comprise a vector capable of replicating within a cell. In particular, the nucleic acid segment may comprise a recombinant vector. A large number of vectors are available commercially and are well known to those in the art, and the selection of such a vector for any number of purposes is also well known and routinely practiced in the art. In general, a vector is compatible with a particular cell type such as prokaryotic, eukaryotic, yeast, plant, insect, etc. The matching of compatible vectors and host cells is well known and routinely practiced in the art. The vector of the present invention may be further defined as comprising the nucleic acid sequence set forth in SEQ ID NO:1, or as a recombinant expression vector capable of expressing an endothelin converting enzyme-2 polypeptide on introduction into a host cell. A preferred vector in the practice of the present invention is the pME18Sf vector.

In certain embodiments, the vector that comprises the nucleic acid segment of the present invention will be an expression vector capable of expressing an endothelin converting enzyme-2 polypeptide on introduction into a host cell. In this embodiment, a nucleic acid segment encoding the endothelin converting enzyme will be transcribed into mRNA and the mRNA may then be translated into a polypeptide. Thus, the recombinant cell will express the ECE-2 polypeptide. The vector in this embodiment will comprise the necessary sequences to express the gene in the particular cell type. For instance the promoter/enhancer regions, translational start sites and downstream signals such as the polyadenylation site if necessary, will be compatible with the host cell transcription/translational mechanisms. Such vectors may also comprise a selectable marker such as an antibiotic resistance gene.

For use in mammalian cells, the control functions of the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The present invention may also be described in certain embodiments as a host cell comprising a recombinant nucleic acid segment that encodes an ECE-2 polypeptide. The recombinant nucleic acid segment may be contained in a vector or it may be integrated into the host genome, and in preferred embodiments, the host cell expresses an endothelin converting enzyme-2. In further preferred embodiments, the vector may comprise SEQ ID NO:1. By "recombinant nucleic acid segment" is meant a segment of nucleic acid that has been removed by man from its naturally occurring position in the genome of its origin and inserted into or joined to a foreign nucleic acid sequence by the techniques of molecular biology. As used herein, the term "engineered" or "recombinant" cell or vector is intended to refer to a cell or vector into which a recombinant gene, such as a gene encoding an endothelin converting enzyme has been introduced. Therefore, engineered cells or vectors are distinguishable from naturally occurring cells or vectors which do not contain a recombinantly introduced gene. Engineered cells or vectors are thus cells or vectors having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Preferred cell lines to be used in the present invention are eukaryotic cells and more preferred are mammalian cells and even more preferably CHO cells. The host cell may be further defined as comprising the nucleic acid segment in accordance with SEQ ID NO:1, positioned in a recombinant vector, although it is understood that the nucleic acid segment may also be integrated into the host genome, and in particular, the host cell may be defined as comprising a recombinant expression vector and expressing a endothelin converting enzyme-2 polypeptide. The host cell may further express the preproET-1 polypeptide. The gene for preproET-1 may be expressed from the same expression vector as the ECE or from a separate recombinant expression vector or even from the host genome.

It is understood that nucleic acid segments that comprise as their nucleic acid sequence, contiguous sequences that are identical to, or are complementary to, corresponding contiguous sequences contained in SEQ ID NO:1 are also encompassed by the present invention. For example, nucleic acid segments comprising a sequence consisting of at least ten, fifteen, twenty, thirty, fifty or sixty contiguous nucleotides that correspond to SEQ ID NO: 1 or its complement are also a part of the present invention. In addition, nucleic acid segments comprising a segment of at least one hundred, one thousand, or even up to 3,291 contiguous nucleotides that correspond to the nucleic acid sequence of SEQ ID NO:1 and including the nucleic acid sequence of SEQ ID NO:1 or its complement are also a part of and are included in the present claimed invention. These contiguous sequences derived from SEQ ID NO:1 or its complement may also be contained in larger nucleic acid molecules of up to 10,000 bases or even up to 5,000, 3,000, 1,000, 500, 100 or even 50 bases. Such nucleic acid segments are well known and routinely used in the art. For example, one may design a primer to be used in an amplification or a sequencing reaction that comprises a contiguous sequence of the present invention joined to sequences derived from a vector, a segment of genomic DNA, polydT or even random priming sequences. In addition, contiguous sequences of the present invention included in vectors such as plasmids, viral vectors, etc. may be used as hybridization probes. In such an embodiment, it is likely that any 15 or more base contiguous sequence of SEQ ID NO:1 may be as useful as any other depending on the application, and therefore all such 15 base or longer contiguous sequences are useful in the practice of the present invention. The nucleic acid segments as defined herein may be RNA molecules or more preferably DNA molecules.

In certain alternate embodiments, the present invention is a partially purified ECE-2 protein, having a specific activity of at least about 275 fmol/30 min/20 µg protein at pH 5.5–5.6 in the ECE assay as described below. In certain preferred embodiments, the ECE-2 protein in the partially purified composition will comprise an amino acid sequence consisting of SEQ ID NO:2. It is also understood that the ECE-2 protein may be fused to a carrier protein or other polypeptide sequence and that all such protein fusions would be encompassed by the present claims. It is also understood that certain portions of the protein sequence, such as the 16 C-terminal residues of SEQ ID NO:2, designated herein as SEQ ID NO:3 for example, or other epitopic sequence derived from SEQ ID NO:2, may be fused to a carrier protein and that such a polypeptide would also be encompassed by the present claims. The polypeptide of the present invention may be isolated from a cell such as a bovine adrenal cortex cell, or it may be a recombinant protein, expressed from an isolated nucleic acid segment. Such expression may be in a cell, such as a eukaryotic or prokaryotic host cell, or it may be expressed in a cell free system such as a rabbit reticulocyte system, for example.

An important use of the polypeptides of the present invention is the production of antibodies which are immunoreactive with said polypeptides. These antibodies will have utility as diagnostic agents for the expression of ECE-2 as well as for use as possible inhibitors of ECE-2 activity. Therefore antibodies which are produced with the peptides or polypeptides of the present invention, or those antibodies which are found to be immunoreactive with the peptides or polypeptides of the present invention, and particularly those that immunoreact with the C-terminal sequence of SEQ ID NO:2 are also encompassed by the present invention. The antibodies may be polyclonal antibodies or monoclonal antibodies, and may be derived from any source such as goat, mouse, bovine, equine, simian or any other source, even including recombinantly produced antibodies. The production of anti-idiotype antibodies is also well known in the art, and any such anti-idiotypic antibodies are also encompassed by the present invention.

An embodiment of the present invention is a method of producing endothelin. The method comprises contacting big endothelin with an endothelin converting enzyme-2 (ECE-2) composition. In certain embodiments, the method also comprises isolated the ET-1. It is known that endothelin converting enzymes have some proteolytic activity for all three forms of big endothelin (endothelin 1, 2 and 3) and that all such activity is encompassed by the present claimed invention. The preferred method is a method of producing endothelin 1 by contacting big endothelin-1 with an endothelin converting enzyme-2. The most preferred enzyme is ECE-2 purified from bovine adrenal cortex, or recombinant ECE-2 expressed from an isolated nucleic acid segment.

An embodiment of the present invention is also a method of producing endothelin-1 (ET-1) in a cell. This method comprises expressing recombinant endothelin converting enzyme in the cell and contacting the endothelin converting enzyme with big endothelin. This method may further comprise isolating the ET-1 produced in the cell. The big endothelin may be expressed in the same cell as the ECE-2, either from an expression vector, such as a recombinant expression vector, or even from the host genome. Expression from the host genome may be from the naturally occurring gene or may be a recombinantly introduced gene. It is also understood that the big endothelin may be introduced exogenously and that the activity would still occur, either on the cell surface or in the interior of the cell and that all such embodiments of the method would be encompassed by the scope and the spirit of the present claimed invention.

An important embodiment of the present invention is a method of screening substances as effectors of endothelin converting enzyme. The discovery of the nucleic acid and amino acid sequences of the present invention provides a new and valuable method of screening naturally occurring and man made substances for their ability to inhibit ECE-2 activity. By the use of the present invention, and particularly by the use of recombinant cells which express the ECE-2, a high throughput assay is possible for the first time. Of particular advantage will be the development of soluble forms of ECE-2 based on the amino acid sequences disclosed herein. Such soluble enzymes will be essentially the hydrophilic regions of ECE-2 that can be secreted into the extracellular medium and thus produced in greater quantity than is possible for a membrane bound enzyme. Such a soluble enzyme will be especially useful for expression in a prokaryotic host cell, such as an *E. coli* cell, for example.

This screening assay comprises obtaining a candidate substance, which can come from any available source. For example, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. In addition, man made substances would also be tested and would include, but are not limited to, synthetic compounds, peptides or other compounds designed de novo based on the predicted protein structure of the ECE. It is also understood that antibodies and other isolated or purified, but naturally occurring compounds could be screened by this process. Recombinant ECE-2 or partially purified ECE-2 is then contacted with the candidate substance in the presence of big endothelin-1, or other endothelin substrate such as big-endothelin-2 or big-endothelin-3, under conditions effective to convert big endothelin-1 to endothelin-1, and measuring the amount of ET-1 produced. The amount of ET-1 produced in the presence of the candidate substance is then compared to the amount of ET-1 produced in an identical reaction without the candidate substance. Cells expressing ECE-2 are then contacted with the candidate substance in the presence of a substrate.

The method of screening substances may also be done in a cell, and in particular in a cell that expresses recombinant ECE-2. In this embodiment, the cell would be contacted with the candidate substance in the presence of the substrate. The substrate may be supplied exogenously, or it may be co-expressed in the cell. Preferred cells to use in this assay are CHO cells.

In the embodiment of the screening process involving a soluble ECE-2, the screening may be done in solution by standard assay methods. Activity would be determined by the concentration of ET-1 in the presence or absence of a candidate substance. The concentration of ET-1 produced might be determined by a sandwich immunoassay, by various protein staining methods or by any other means known in the art.

In an alternative method, recombinant cells expressing ECE-2 would be deposited on a surface such as the wells of a microtiter plate or in any suitable medium or container. A big endothelin substrate would also be present, either produced by the cells or supplied exogenously. Some distinguishable groups of cells would then be exposed to the candidate substance and some would not be so exposed under conditions effective to convert big ET-1 to ET-1. A measurement of the production of ET would then be compared between cells which were or were not incubated with the candidate substance. A decrease in ET concentration over the control would indicate an inhibitor. Preferred cells to be used in the assay would be Chinese hamster ovary cells (CHO) for example, however, any cells which express the ECE-2 would be acceptable and would be encompassed by the present claimed invention. Examples of other cell types include MDCK, $CaCo_2$, BHK, COS AND 293 cells.

Alternatively, candidate substances could be screened with the use of reporter genes under the control of endothelin converting enzyme-2 promoters. In this embodiment, the reporter gene would be expressed in both the presence and absence of a candidate substance as in the previously described screening assays. A change in level of the reporter gene product in the presence of the candidate substance relative to the level in the absence of the candidate substance would indicate an effector of ECE expression. Preferred reporter genes include, but are not limited to the β-galactosidase gene from E. coli and chloramphenicol acetyltransferase.

With the availability of a cDNA encoding an active endothelin converting enzyme-2, it is now possible to express large amounts of the enzyme in cultured cells. This ability will allow the molecular mechanism of the protease activity to be elucidated. This information will be crucial for the design of inhibitors and possibly useful mutations of the enzyme. The design and production of such mutant enzymes by site directed mutagenesis are well known in the art and such mutant enzymes would also be encompassed by the present claims.

A method of producing recombinant ECE-2 (rECE-2) is also an embodiment of the present invention. This method comprises obtaining an expression vector comprising a contiguous nucleic acid segment encoding the amino acid sequence of SEQ ID NO:2 operatively linked to a promoter and expressing the nucleic acid segment to produce recombinant ECE-2. By "operatively linked" to a promoter is meant that the gene to be expressed in linked downstream (3') of a promoter sequence at an appropriate distance so that transcription may be initiated at the promoter site and the polymerase enzyme will read through the gene to be expressed. The promoter may be a heterologous promoter as defined above, or it may be a natural ECE-2 promoter. This method may be done in a cell such as a recombinant cell that expresses rECE-2, and preferably a CHO cell, or it may be done in a cell free system. The method may further comprise the step of isolating the ECE-2 so produced.

The abbreviations used throughout the present disclosure are: ET, endothelin; ECE, endothelin converting enzyme; APMSF, 4-amidinophenylmethylsulphonyl fluoride; pCMS p-chloromercuriphenylsulphonic acid; NEM, N-ethylmaleimide; MES, 2-[N-morpholino] ethanesulfonic acid; EIA, enzyme immunoassay; RT-PCR, reverse transcription-polymerase chain reactions; RACE, rapid amplification of cDNA ends.

DETAILED DESCRIPTION OF THE PREFERRED EMBODIMENTS

Figure 1A:
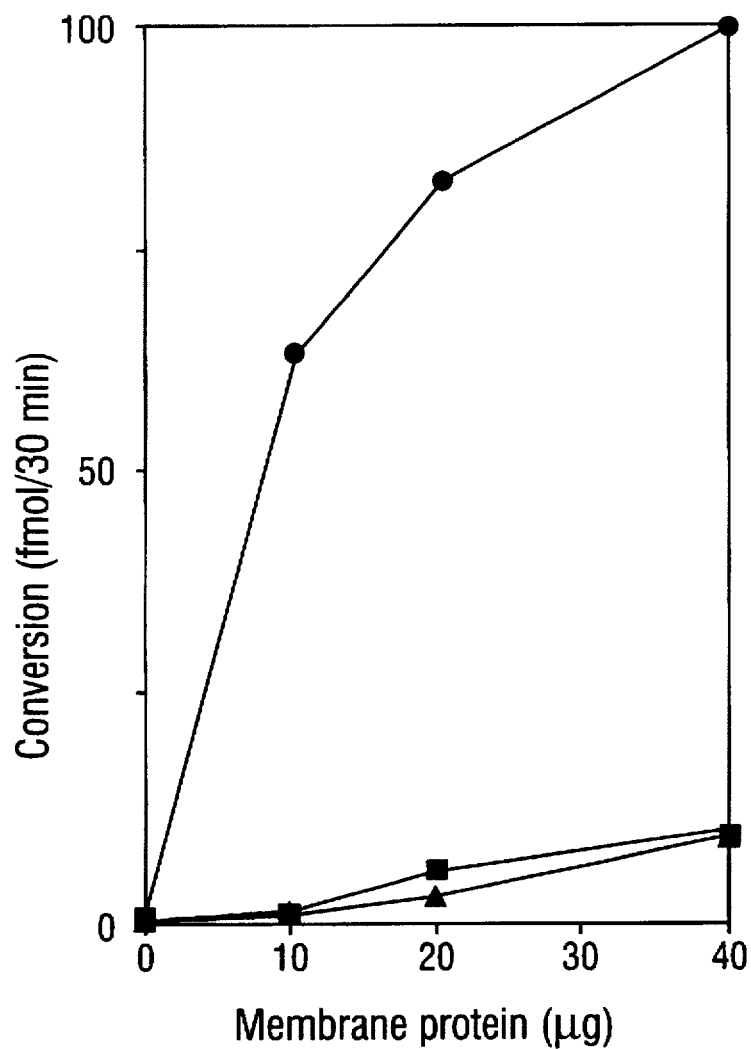
FIG. 1A. Isopeptide substrate selectivity of ECE-2. Substrates are: closed circles, big ET-1 (1–38); closed squares, big ET-2 (1–38); and closed triangles, big ET-3 (1–41 Amide). Activity is reported as conversion (fmol/30 min) vs µg of membrane protein.

The present invention arises frown the cloning of a gene encoding ECE-2, a novel metalloprotease that converts big ET-1 into mature ET-1 both in vitro and in transfected cells. ECE-2 qualifies as an "endothelin converting enzyme" in that it produces large amounts of mature ET-1 from big ET-1 in test tubes and in live cells (up to 40% of total endothelin peptides has been converted in double-transfection assays). However, it is not determined whether ECE-2 cleaves big endothelins at other site(s) than the Trp21-Val/Ile22 cleavage site.

Although ECE-2 closely resembles ECE-1, the two enzymes exhibit two significant differences: (i) the nanomolar sensitivity of ECE-2 to phosphoramidon in vitro resembles NEP rather than ECE-1 (Roques et at., 1993); (ii) the acidic pH optimum of ECE-2 with a narrow pH profile is unusual for a metalloprotease. Although a pH optimum of 5.3–5.5 has been reported for a class of matrix metalloprotease in cartilage, matrix metalloproteinase-3 (MMP-3; stromelysin-1), this enzyme shows a broad pH profile spanning a pH range from 5 to >8 (Wilhelm et al., 1993). The present inventor is unaware of a metalloprotease that is inactive at neutral pH. However, ECE-1 and ECE-2 have very similar isopeptide substrate selectivities; both enzymes strongly prefer big ET-1 over big ET-2 and -3.

Although ECE-2 cannot efficiently convert extracellular big ET-1 on the cell surface, as expected from the acidic pH profile of the enzyme, double transfection of CHO cells with ECE-2 and preproET-1 led to a significant production of mature ET-1, due to an intracellular cleavage of endogenously synthesized big ET-1 in these cells. The deduced structure of ECE-2 predicts that it is expressed as a type II integral membrane protein, and its C-terminal catalytic domain faces the lumen of secretory vesicles where it encounters the substrate big ET-1. The trans-Golgi network (and later compartments of the secretory pathway) are known to provide a highly acidified intravesicular environment in many cells (Anderson and Orci, 1988). The luminal pH of the trans-Golgi network has been directly measured to be 5.5–5.7, which precisely matches the optimal pH range of ECE-2. Therefore, it is contemplated that ECE-2 functions in these acidified compartments of the secretory pathway. It is further contemplated that if ECE-2 is expressed on the cell surface, it may not have functional relevance except under pathological conditions where the interstitial space is abnormally acidified. Small but detectable amounts of mature ET-1 were produced in the CHO/ECE-2-CHO/preproET-1 coculture experiments (FIG. 3), but the inability of the two ECE inhibitors to inhibit this conversion at low concentrations suggested that the conversion occurred intracellularly. The small amounts of conversion observed in the CHO/ECE-2-CHO/preproET-1 cocultures may be due, therefore, to an internalization of the extracellular big ET-1 by the CHO/ECE-2 cells, followed by cleavage within the acidified intracellular vesicles and then re-secretion of the mature peptide.

Although the physiological relevance of the intracellular versus cell surface conversion of big endothelins by the ECE isoenzymes is not completely understood, the discovery of an intracellular ECE-2 as disclosed herein indicates that the development of ECE inhibitors requires a careful consideration of cell permeability of inhibitor compounds. The live cell assay system described herein will therefore be useful in the screening of therapeutically useful ECE inhibitors.

The isolation of the ECE-2 encoding cDNA of the present invention will allow the expression of large quantities of ECE-2 in various expression vectors and host cells. Examples of appropriate expression systems include, but are not limited to, bacterial expression of recombinant plasmids and/or phage, yeast cells, recombinant baculovirus-infected insect cells and mammalian tissue culture cell such as Chinese hamster ovary (CHO) cells, or even cell free expression systems. The ECE-2 cDNA may also be used for stable expression of the enzyme in transgenic animals such as mice. The engineering of DNA segment(s) for expression in a prokaryotic or a eukaryotic system may be performed by techniques generally known to those of skill in recombinant expression. Such techniques may employ promoters/enhancers, ribosomal binding sequences, polyadenylation sites, etc. in the effective positions relative to the sequence to be expressed. Expression vectors are readily available from commercial sources that contain the necessary control sequences so that the sequence to be expressed may be easily inserted in the correct position and orientation.

Prokaryotic hosts may be preferred for expression of ECE-2 for some applications, and in particular for the expression of soluble forms of the enzyme. Some examples of prokaryotic hosts are various *E. coli* strains, bacilli such as *Bacillus subtilis*, or other enterobacteriaceae such as *Salmonella typhimurium* or *Serratia marcescens*, or various Pseudomonas species may be used, however *E. coli* is the most preferred prokaryotic host.

In general, plasmid vectors containing replicon and control sequences which are derived from species compatible with the host cell are used with each particular host. The vector ordinarily carries a replication site, as well as marking sequences which are capable of providing phenotypic selection in transformed cells. For example, a well known plasmid useful for transforming *E. coli* is pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, phage lambda derived vectors are readily available and may be utilized to transform host cells, such as various *E. coli* strains. The most preferred prokaryotic vectors include pKK233-2, which utilizes the strong IPTG-inducible $P_{trc}$ promoter and the pT7 series which utilize the T7 RNA polymerase promoter system.

Some promoters commonly used in recombinant DNA construction include the B-lactamase (penicillinase) and lactose promoter systems, as well as viral promoters. While these are the most commonly used, other microbial promoters have been discovered and utilized, and details concerning their nucleotide sequences are readily available, enabling a skilled worker to ligate them functionally into plasmid vectors.

In addition to prokaryotes, eukaryotic microbes, such as yeast cultures may also be used. *Saccharomyces cerevisiae*, or common baker's yeast is a commonly used eukaryotic microorganism, although a number of other strains are available. For expression in Saccharomyces, the plasmid YRp7, for example, may be used. This plasmid contains the trp1 gene which provides a selection marker for a mutant strain of yeast lacking the ability to grow in tryptophan. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the expressed sequence to provide polyadenylation of the mRNA and termination. Other promoters that have the additional advantage of transcription controlled by growth conditions include, but are not limited to the promoter region for alcohol dehydrogenase 2, isocytochrome C, acid phosphatase, degradative enzymes associated with nitrogen metabolism, the aforementioned glyceraldehyde-3-phosphate dehydrogenase, and enzymes responsible for maltose and galactose utilization.

One may also use insect cells as a host for baculoviral expression vectors containing the ECE-2 encoding sequence. Currently, the preferred baculovirus expression systems utilize the lytic insect virus known as *Autographa californica* multiply enveloped nuclear polyhedrosis virus. For production of recombinants in insect cells using recombination baculoviral vectors, it is desirable to utilize the polyhedron gene's powerful promoter and control sequences. This can be accomplished by replacing the baculoviral polyhedron gene with the cDNA to be expressed. Baculoviral expression vectors ordinarily include all the original baculoviral genes except the polyhedron gene and may include additional marker genes such as the β-galactosidase gene. After cloning the cDNA to be expressed in a suitable transfer plasmid, the cDNA can be transferred in place of the baculovirus polyhedron gene by the process of recombination. The transfer plasmids contain baculoviral DNA sequences to promote the recombination with linear baculoviral DNA and may also contain additional marker genes such as the β-galactosidase gene. Suitable transfer plasmids include pBlueBac III, pBlueBacHis, and pAcUW21. The recombination to assemble the recombinant baculovirus which expresses the cDNA of interest and production of the protein product from that cDNA is performed in insect cells or insect hosts. Examples of suitable host cells include *Spondoptera frugiperda* Sf9 cells, Sf21 cells, and MG1 cells.

In addition to microorganisms and insects, cultures of cells derived from vertebrate organisms may also be used as hosts. In principle, any such vertebrate or invertebrate cell culture is workable. However, vertebrate cells are a preferred host, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines, with CHO cells being the most preferred. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

When used in mammalian cells, the control functions on the expression vectors are often provided by viral material. For example, commonly used promoters are derived from polyoma, cytomegalovirus, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit which includes the ECE-2 protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that ECE-2 of the present invention may be "overexpressed", i.e., expressed in increased levels relative to its natural expression in endothelial cells, or even relative to the expression of other proteins in the recombinant host cell. Such overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural endothelial cells is indicative of overexpression, as is a relative abundance of the specific protein in relation to the other proteins produced by the host cell as determined, e.g., by visibility on a gel.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Amino Acid Segments

An important embodiment of the amino acid sequences of the present invention is the use of the ECE-2 amino acid sequence to model the protein structure for use in inhibitor design, for example. Initially, this entails a comparison of the protein sequence disclosed herein with the sequences of related proteins to predict transmembrane regions, zinc binding regions and even the protease catalytic site. In this way, the transmembrane domains and the putative glycosylation sites have been determined. Also, by comparing the amino acid sequence of the present disclosure with proteins of similar function (membrane bound metalloproteases) sequences may be identified which are directly involved in those functions. In particular, amino acid residues which are conserved over a range of species are good candidates for involvement in functional active sites or binding sites. The amino acid sequence of the endothelin converting enzyme will thus be useful for designing superior inhibitors. For example, potential inhibiting substances can be tested for binding to amino acid segments known to be involved in various functions of the protease, and would thus be screened for potential inhibition of activity.

An alternate use of the ECE-2 protein sequence will be to model the protein structure for use in designing compounds as vehicles for drug targeting. For example, analogs of big endothelin may be designed and used as targeting agents to direct drug delivery specifically to the endothelium.

Production of Antibodies

Another important embodiment of the amino acid sequences of ECE-2 is their use in the production of antibodies. This amino acid sequence may be used to synthesize peptide antigens for monospecific antibody development. Peptides of 4 to 6 to 10 or even 20 or more amino acids derived from SEQ ID NO:2 either randomly selected by sequence "walking" for example, or peptides chosen by criteria based on predicted hydrophilic regions of the native protein may be used for the production of antibodies. Antibodies, both polyclonal and monoclonal, specific for ECE-2 of the present invention may be prepared using conventional immunization techniques, as will be generally known to those of skill in the art. A composition containing antigenic epitopes of the ECE-2 protein can be used to immunize one or more experimental animals which will then proceed to produce specific antibodies against ECE-2. Typically an animal used for production of antisera is a rabbit, a mouse, a rat, a hamster or a guinea pig. Because of the relatively large blood volume of rabbits, a rabbit is a preferred choice for production of polyclonal antibodies.

Polyclonal antisera may be obtained, after allowing time for antibody generation, simply by bleeding the animal and preparing serum samples from the whole blood.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH), Purified Peptide Derivative of Tuberculin (PPD) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimyde and bis-biazotized benzidine. As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used in the production of polyclonal antibodies depends inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various time points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No. 4,196,265, incorporated herein by reference. Typically, a technique involves first immunizing a suitable animal with a selected antigen (e.g., a polypeptide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell, and a more preferred cell line is the NS1/1 Ag 4.1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established. Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in selection medium such as HAT media (hypoxanthine, aminopterin, thymidine). Unfused myeloma cells lack the enzymes necessary to synthesize nucleotides from the salvage pathway and are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides of the invention can be recognized as antigens, and thus identified. Once identified, those polypeptides can be isolated and purified by techniques such as antibody-affinity chromatography. In antibody-affinity chromatography, a monoclonal antibody is bound to a solid substrate and exposed to a solution containing the desired polypeptide. The polypeptide-antigen is removed from the solution through an immunospecific reaction with the bound antibody. The polypeptide is then easily removed from the substrate and purified.

It is proposed that the monoclonal antibodies of the present invention will find useful application in standard immunochemical procedures, such as ELISA and Western blot methods, as well as other procedures which may utilize antibody specific to ECE-2 epitopes. Additionally, it is proposed that monoclonal antibodies specific to the particular ECE-2 epitopes may be utilized in other useful applications. For example, their use in immunoabsorbent protocols may be useful in purifying native or recombinant endothelin converting enzymes from various species or variants thereof. A particularly useful application of such antibodies is in purifying native or recombinant endothelin converting enzymes, for example, using an antibody affinity column. Such antibodies would also be useful as immunohistochemical or immunoblotting reagents in the diagnosis of hypertension and related diseases. The operation of all such immunological techniques will be known to those of skill in the art in light of the present disclosure.

Nucleic Acid Hybridization

The DNA sequences disclosed herein will find utility as probes or primers in nucleic acid hybridization embodiments. As such, it is contemplated that oligonucleotide fragments corresponding to the sequences of SEQ ID NO:1 for stretches of between about 15 to 17 nucleotides for probing less complex libraries, to about 30 nucleotides to probe or prime in highly complex libraries will find particular utility, with even longer sequences, e.g., 40, 50, 100, even up to full length, being more preferred for certain embodiments. The ability of such nucleic acid probes to specifically hybridize to ECE-2 coding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1 will also have utility as hybridization probes. These probes will be useful in a variety of hybridization embodiments, such as Southern and Northern blotting in connection with analyzing ECE-2 structural or regulatory genes in diverse tissues and in various species. The total size of the fragment, as well as the size of the complementary stretches, will ultimately depend on the intended use or application of the particular nucleic acid segment. Smaller fragments will generally find use in hybridization embodiments, wherein the length of the complementary region may be varied, such as between about 15 and about 100 nucleotides, or even up to the full length sequence according to the complementary sequences one wishes to detect.

The use of a hybridization probe of about 15–17 nucleotides in length allows the formation of a duplex molecule that is both stable and selective. Molecules having complementary sequences over stretches greater than 17 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of ECE-2 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and or high temperature conditions, such as provided by 0.02M–0.15M NaCl at temperatures of 50° C. to 70° C. Such selective conditions tolerate little, if any, mismatch between the probe and the template or target strand.

Preferred hybridization conditions and temperatures include a solution containing 50% (volume/volume) formamide, 5X Denhardt's solution, 6X SSC, 0.1% (weight/volume) SDS, and 100μg/ml salmon sperm DNA, and 1 mM sodium pyrophosphate at 37° C. For nucleotide sequences longer than 50 nucleotides, preferred wash conditions include a solution containing 2X SSC/0.5% SDS at 25° C. for 30 min followed by one or more washes in a solution containing 0.2X SSC/0.5% SDS at 60° C. for 30 min per wash. For nucleotide sequences shorter than 50 nucleotides, preferred wash conditions include a solution containing 2X SSC/1% SDS at 25° C. for 30 min followed by one or more washes in a solution containing 2X SSC/1% SDS at 50° C. for 30 min.

Of course, for some applications, for example, where one desires to prepare mutants employing a mutant primer strand hybridized to an underlying template or where one seeks to isolate ECE-2 encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the circumstances based on the particular criteria required (depending, for example, on the G+C contents, type of target nucleic acid, source of nucleic acid, size of hybridization probe, etc.). Following washing of the hybridized surface to remove nonspecifically bound probe molecules, specific hybridization is detected, or even quantified, by means of the label.

Longer DNA segments will often find particular utility in the recombinant production of peptides or protein. DNA segments which encode peptide antigens from about 15 to about 50 amino acids in length, or more preferably, from about 15 to about 30 amino acids in length are contemplated to be particularly useful, as are DNA segments encoding entire ECE-2 proteins.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any reasonable length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid sequence of SEQ ID NO:1 or to the amino acid sequence of SEQ ID NO:2. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology as discussed below, in which changes in the protein structure may be engineered, based on considerations of the properties of the amino acids being exchanged.

DNA segments encoding an ECE-2 gene may be introduced into recombinant host cells and employed for expressing an ECE protein. Alternatively, through the application of genetic engineering techniques, subportions or derivatives of selected ECE genes may be employed. Equally, through the application of site-directed mutagenesis techniques, one may re-engineer DNA segments of the present invention to alter the coding sequence, e.g., to introduce improvements to the antigenicity of the protein or to test for binding site mutants in order to examine protease activity at the molecular level. Where desired, one may also prepare fusion peptides, e.g., where the ECE coding regions are aligned within the same expression unit with other proteins or peptides having desired functions, such as for immunodetection purposes.

In a further embodiment, the nucleic acid sequences of the present invention may be used to synthesize anti-sense or ribozyme probes to down-regulate expression of the endothelin converting enzyme in the endothelium for use as vasoconstrictor control agents. For example, an anti-sense probe that is designed to hybridize to the mRNA synthesized from the ECE-2 gene would, when introduced into the endothelial cells, disrupt translation of the mRNA and would hence lower the expression of the ECE-2 protein. The lowered levels of ECE-2 would function to lower mature endothelin levels.

Biological Functional Equivalents

Modification and changes may be made in the structure of the encoded polypeptides used in the vectors and DNA segments of the present invention and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the proteins, or corresponding DNA sequences which encode said proteins without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

Screening Assays

In still further embodiments, the present invention concerns a method for identifying new endothelin converting enzyme inhibitory compounds and particularly those that inhibit ECE-2, and which may be termed "candidate substances." It is contemplated that this screening technique will prove useful in the general identification of any compound that will serve the purpose of inhibiting endothelin maturation. It is further contemplated that useful compounds in this regard will in no way be limited to pre-endothelin analogs.

Accordingly, in screening assays to identify pharmaceutical agents which affect endothelin maturation, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be anti-ECE-2 antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

To identify a candidate substance capable of inhibiting ECE proteolytic activity, one would first obtain a recombinant cell line capable of expressing ECE or would obtain a soluble form of ECE. Naturally, one would measure or determine the activity of the ECE protease in the absence of the added candidate substance. One would then add the candidate substance to the assay mix or cell growth media or one would expose the cells in an appropriate way to the candidate substance and re-determine the ability of the cells to produce mature endothelin in the presence of the candidate substance. A candidate substance which reduces the activity of the ECE-2 protease relative to the activity in its absence is indicative of a candidate substance with inhibitory capability. The indicator in the screening assays will preferably be mature endothelin.

In the most preferred embodiment, stably transfected ECE over-expressing cell lines will be used for high throughput assays to screen synthetic compounds, fungal extracts, plant extracts, bacterial extracts, higher eukaryotic cell extracts or others as mentioned above, for potential inhibitors of the ECE activity. In addition, these various extracts will be screened for use in the treatment of disorders such as high blood pressure, kidney failure and certain forms of stroke. Screening assays described in Sawamura et al., 1991 and Arai et al., 1993, (both incorporated herein by reference) may also be used in the practice of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cloning of ECE-2 cDNA

The N-terminal sequence of one of the Lys-C-digested peptide fragments from the purified ECE-1 (residues 562–586, Xu et al., 1994) showed a significant similarity to amino acid residues 543–567 of human NEP (Malfroy et al., 1988). A pair of highly degenerate oligonucleotide primers was designed based on this 25-residue sequence. Reverse transcription-polymerase chain reactions (RT-PCR) from bovine adrenal cortex RNA yielded cDNA products of the predicted size. These cDNA fragments were subcloned into plasmid vectors and the nucleotide sequence was determined. Unexpectedly, the sequences from several randomly picked plasmid clones revealed that the 75-bp cDNA product was a mixture of two distinct cDNA sequences: about 80% of the plasmid clones encoded the ECE-1 microsequence, whereas the nucleotide sequences from the remaining clones predicted a closely related polypeptide sequence in which 4 amino acid residues out of 25 differed from ECE-1. Moreover, the third nucleotide residues in the reading frame were frequently different between the two cDNA sequences, suggesting that these cDNAs are derived from the products of two different genes. Based on these findings, the second putative protein was designated ECE-2.

A cDNA library from bovine adrenal cortex was screened with the cloned ECE-2 RT-PCR product as probe. In an initial screening, 9 ECE-2 positive clones were detected, as compared with 15 ECE-1 clones detected from the same library. Partial sequencing of these clones indicated that they contained overlapping cDNAs derived from the same ECE-2 mRNA, but lacked a 5' part of the coding region. Since the 5' part of the cDNA could not be cloned by rescreening the library, a rapid amplification of 5' cDNA ends (5'-RACE) was performed using a nested set of specific internal primers. This yielded overlapping 5' extensions to the cDNA, which covered all of the coding sequence. The full-length nucleotide sequence of the ECE-2 cDNA revealed a 5' ATG triplet which was preceded by an in-frame stop codon and followed by a long open-reading frame. The predicted amino acid sequence of ECE-2 is designated herein as SEQ ID NO:2.

Structure of ECE-2

The ECE-2 cDNA sequence encodes a novel 787-amino-acid polypeptide, which shares important structural features with ECE-1: (i) The cDNA predicts a type II integral membrane protein with an 82-residue N-terminal cytoplasmic tail, 23-residue putative transmembrane helix, and a large (682 residue) extracellular C-terminal region. (ii) The extracellular portion of ECE-2 constitutes the putative catalytic domain, and contains (residues 622–630) a highly conserved consensus sequence of a zinc-binding motif, $\phi$ XHE$\phi$ $\phi$ H$\phi$ $\Psi$ (where $\phi$ and $\Psi$ represent uncharged and hydrophobic amino acids, respectively), that is shared by many $Zn^{2+}$ metalloproteases (Rawlings and Barrett, 1993). (iii) ECE-2 has 10 predicted sites for N-glycosylation in the extracellular domain, suggesting that ECE-2, like ECE-1 (Shimada et al., 1994), is a highly glycosylated protein.

Immunoblot analysis with an anti-ECE-2 C-terminal peptide antiserum shows that ECE-2 is expressed as a ≈130 kDa protein in bovine adrenal medulla. The predicted molecular weight of the ECE-2 polypeptide is 88952. The difference between this value and the apparent molecular weight of ECE-2 on immunoblots may be largely due to the sugar side chains. (iv) There are 4 Cys residues in the extracellular domain near the transmembrane helix, that are conserved among all proteins in the NEP-ECE-Kell family.

A search of the Entrez sequence database detected a similarity of the ECE-2 sequence to ECE-1, NEP and the human Kell minor blood group protein (Lee et al., 1991). The sequence similarity is especially high within the C-terminal one third of the putative extracellular domain, including the region around the zinc-binding motif. Within this region (amino acids 582–787 of ECE-2), the identities of ECE-2 with respect to ECE-1, NEP and Kell are 71%, 44% and 40%, respectively. ECE-1 and ECE-2 are 52% identical to each other in the N-terminal portions (amino acids 1–581 in ECE-2), while they resemble NEP and Kell only slightly in these regions. This indicates that ECE-1 and ECE-2 comprise a subfamily within this group of type II membrane-bound metalloproteases.

Tissue Distribution of ECE-2 mRNA-Northern blot analysis of bovine tissues revealed relatively large amounts of the 3.3-kb ECE-2 mRNA in the neural tissues, i.e., cerebral cortex, cerebellum and adrenal medulla. Small amounts of the 3.3-kb mRNA were detected also in myometrium and testis. Low amounts of a longer mRNA (≈4.7 kb) were detected in ovary and cultured endothelial cells, as well as in the aforementioned neural tissues. A long (96-h) exposure of the blots showed that the 4.7-kb mRNA is expressed at very low levels in many other tissues. Screening of an endothelial cell cDNA library confirmed that the 4.7-kb species is an authentic ECE-2 mRNA with an extended 3'-noncoding region. The coding sequences of the 3.3-kb and 4.7-kb mRNA were identical. In all tissues examined, the absolute amounts of ECE-2 mRNAs were much smaller than the ECE-1 mRNA. The intensity of the ECE-1 mRNA signals in similar northern blots were several fold higher than that for ECE-2 mRNA even in the brain, where ECE-1 mRNA expression is comparatively low (Xu et al., 1994). In cultured endothelial cells, the amount of ECE-2 mRNA is estimated to be only 1–2% of that of ECE-1 mRNA.

In Vitro Characterization of ECE-2

CHO cells do not possess detectable levels of endogenous ECE activity, assayed both in vitro and in live cells (Xu et al., 1994). By transfecting an ECE-2 expression construct driven by the SRα vital promoter (Sakamoto et al., 1993), a stable transfectant cell line was generated, CHO/ECE-2. Immunoblot analysis showed that membrane fractions from CHO/ECE-2 and CHO/ECE-1 (Xu et al., 1994) cells contain high levels of ECE-2 and ECE-1 proteins, respectively, and that the antisera to the respective C-terminal peptides did not cross-react. In addition, preliminary digestions with endoglycosidase H and F showed that the ≈110 kDa species seen in the transfected cells are partially glycosylated enzymes. To compare the enzymological properties of ECE-1 and ECE-2, the membrane-associated ECE activities from these cell lines were assayed in parallel. Initial studies using standard ECE-1 assay conditions detected little ECE activity in multiple ECE-2 transfectant clones, which had been confirmed to express high levels of ECE-2 mRNA by Northern and immunoblot analyses. This data led to the surprising discovery that ECE-2 is virtually inactive at the neutral pH (6.8) used in the standard ECE-1 assay.

Figure 1B:
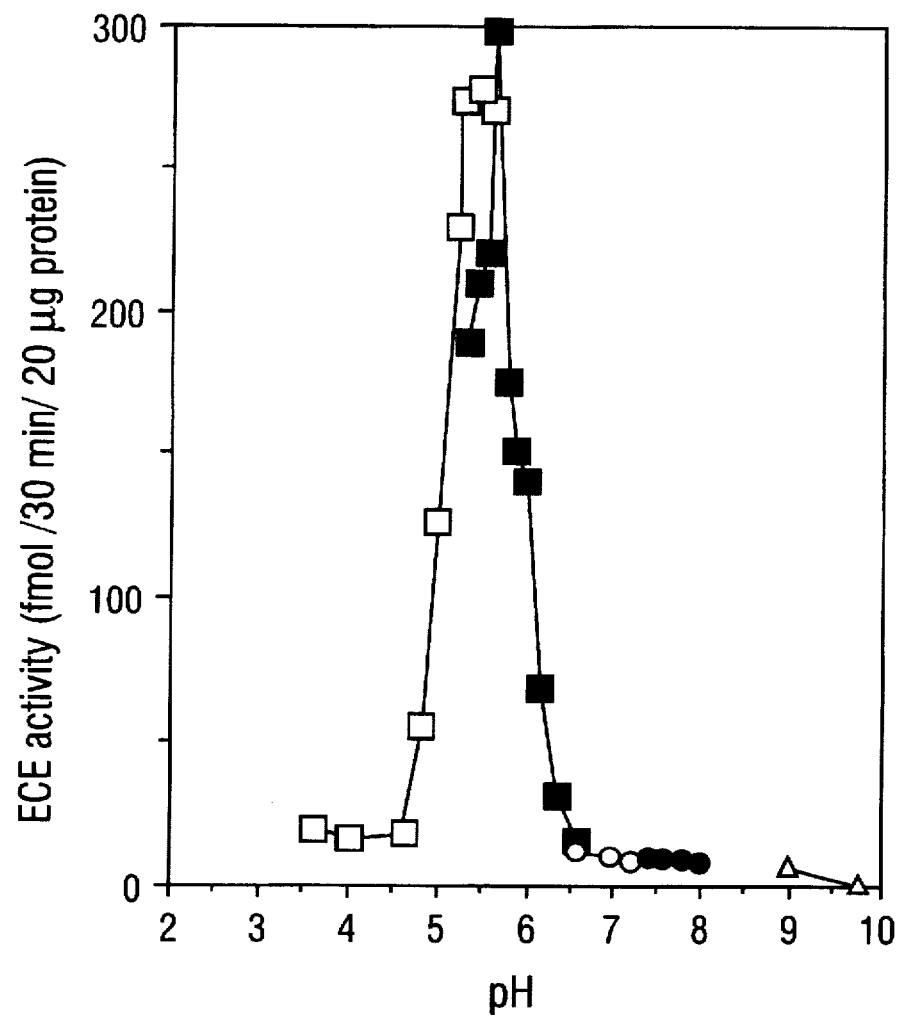
FIG. 1B. pH profile of ECE-2. Graph shows ECE-2 activity measured as fmol/30 min/20 µg protein over a range of pH. Buffers are: open squares, acetate; closed squares, MES; open circles, phosphate; closed circles, Tris; open triangles, glycine.

FIG. 1B is a pH profile of ECE-2. Optimal activity of ECE-2 is at pH 5.5 in contrast to the previously discovered ECE-1, which has optimal activity at pH 6.8. Both enzymes have a sharp pH dependency and one enzyme is virtually inactive at the optimal pH for the other. In all subsequent studies, ECE-2 assays were performed at pH 5.5. Crude membranes from untransfected CHO cells did not have a detectable ECE activity as assayed either at pH 5.5 or 6.8. A majority of the ECE-2 activity in the CHO/ECE-2 cell homogenates was found in the membrane fraction. No significant ECE-2 activity was detected in the culture supernatants from CHO/ECE-2 cells.

Table 2 compares the sensitivity of ECE-1 and ECE-2 to various protease inhibitors. Both enzymes are inhibited by metal chelating agents, the metalloprotease inhibitor phosphoramidon, and the specific ECE inhibitor FR901533. They are not inhibited by the specific NEP inhibitor thiorphan, the angiotensin converting enzyme inhibitor captopril, or inhibitors of other classes of proteases. The organic mercury thiol reagent pCMS apparently augmented the activity of ECE-2 in this crude membrane-based assay system. This may be due to the inhibition of thiol protease(s) which act to degrade the product ET-1 (and/or ECE-2 protein) under the acidic pH used in our ECE-2 assay.

Figure 1C:
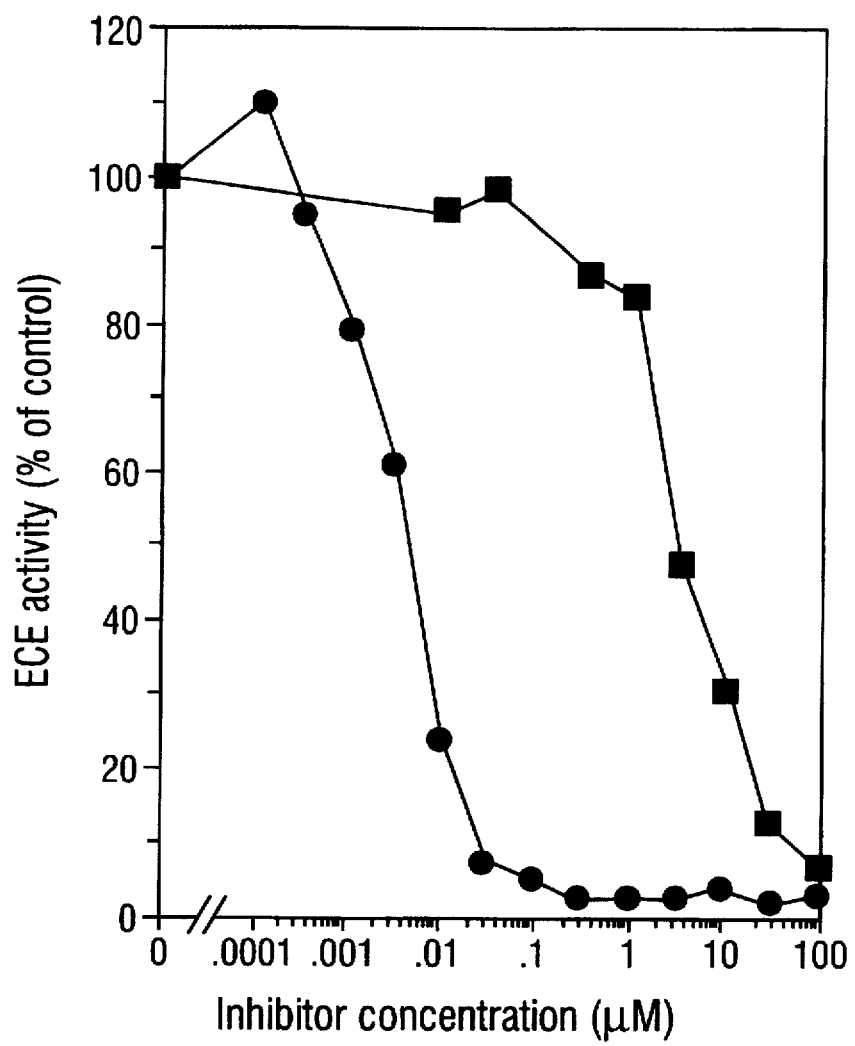
FIG. 1C. Concentration dependent inhibition of ECE-2 by phosphoramidon (closed circles) and FR901533 (closed squares). ECE activity is shown as % of control.

Although ECE-1 and ECE-2 show a similar overall profile of inhibitor sensitivity, dose-response analysis of the inhibition by phosphoramidon and FR901533 demonstrate a striking pharmacological difference between ECE-1 and ECE-2. The inhibition profile of ECE-2 is shown in FIG. 1C. The potency of phosphoramidon against ECE-2 is ≈250-fold higher than against ECE-1 ($IC_{50}$ values: 1 µM and 4 nM for ECE-1 and ECE-2, respectively). In contrast, FR901533 inhibits both enzymes with similar potencies ($IC_{50}$ values: 2 µM and 3 µM for ECE-1 and ECE-2, respectively). Phosphoramidon is a competitive inhibitor for this family of metalloproteases (Opgenorth et al., 1992). In order to confirm that the observed difference in the apparent $IC_{50}$ values for phosphoramidon is not due to a large difference in substrate affinity between ECE-1 and ECE-2, $K_m$ values were determined for the substrate by measuring the initial rate of cleavage under increasing concentrations of big ET-1 (0.01–10 µM). The apparent $K_m$ values of ECE-1 and ECE-2 were both within 1–2 µM ranges as determined with 20 µg crude membrane proteins per reaction (30 min incubation).

TABLE 2

Protease inhibitor profile of ECE from solubilized CHO/ECE-1 and CHO/ECE-2 membranes

| Inhibitor (100 µM) | ECE-1[a] | ECE-2[a] |
|---|---|---|
| (−) (Control) | 100 | 100 |
| EDTA | 6 | 8 |
| 1,10-Phenanthroline | 5 | 7 |
| Phosphoramidon | 7 | 8 |
| PR901533 | 7 | 10 |
| Thiorphan | 77 | 105 |
| Captopril | 114 | 84 |
| APMSF[b] | 107 | 93 |
| Leupeptin | 105 | 84 |
| Pepstatin A | 94 | 99 |
| E-64 | 83 | 94 |
| pCMS | 136 | 345 |
| N-Ethylmaleimide | 120 | 76 |

[a]Percent ECE activity without inhibitor.
[b]4-Amidinophenylmethylsulfonyl fluoride.

FIG. 1A shows the isopeptide substrate selectivity of ECE-2. Like ECE-1, ECE-2 has a strong substrate preference towards big ET-1 at its optimal pH. As determined with 20–40 µg membrane proteins, ECE-1 cleaves big ET-2 and big ET-3 only 5–7% and 1–3% as rapidly as it converts big ET-1, respectively. Similarly, ECE-2 cleaves big ET-1, -2 and -3 at relative rates of 100%: 7–10%: 4–9%. To confirm that this apparent selectivity towards big ET-1 is not due to a difference in the stability of isopeptide substrates or products during the enzyme reactions, each big and mature peptide (0.1 µM) were incubated with 20 µg crude membrane proteins under the standard ECE-1 and ECE-2 assay conditions, and the amount of the remaining intact peptide was measured after incubation. The reaction mixture did not contain protease inhibitors, although APMSF, pCMS and pepstatin A was included in the initial homogenization buffer for membrane preparation as previously described (Xu et al., 1994).

Under the ECE-1 assay conditions (pH 6.8), no significant degradation of either of the big and mature isopeptides was detected after up to 4 hours incubation. In contrast, appreciable degradation of the substrates and products were observed under the ECE-2 assay conditions (pH 5.6); after incubation for 30 min (standard assay period) the amounts of intact peptides decreased by approximately 15%, and after 2 h incubation, the remaining amounts of intact peptides were 50–55%. Importantly, however, no appreciable difference was observed in the rate of degradation among the different isopeptides; big ET-1, -2, -3 and mature ET-1, -2, -3 were all degraded at similar rates. Crude membranes from CHO/ECE-2 and untransfected CHO cells exhibited similar rates of degradation, indicating that the degradation is caused by endogenous acidic protease(s) contained in the CHO membrane preparations. These findings indicate that the >10-fold isopeptide selectivity observed in the specific cleavage of big peptides by ECE-1 and ECE-2 is not an artifact due to a selective degradation of the isopeptide substrate or product.

Cleavage of Big ET-1 by Live ECE-2-Transfected Cells

Figure 2:
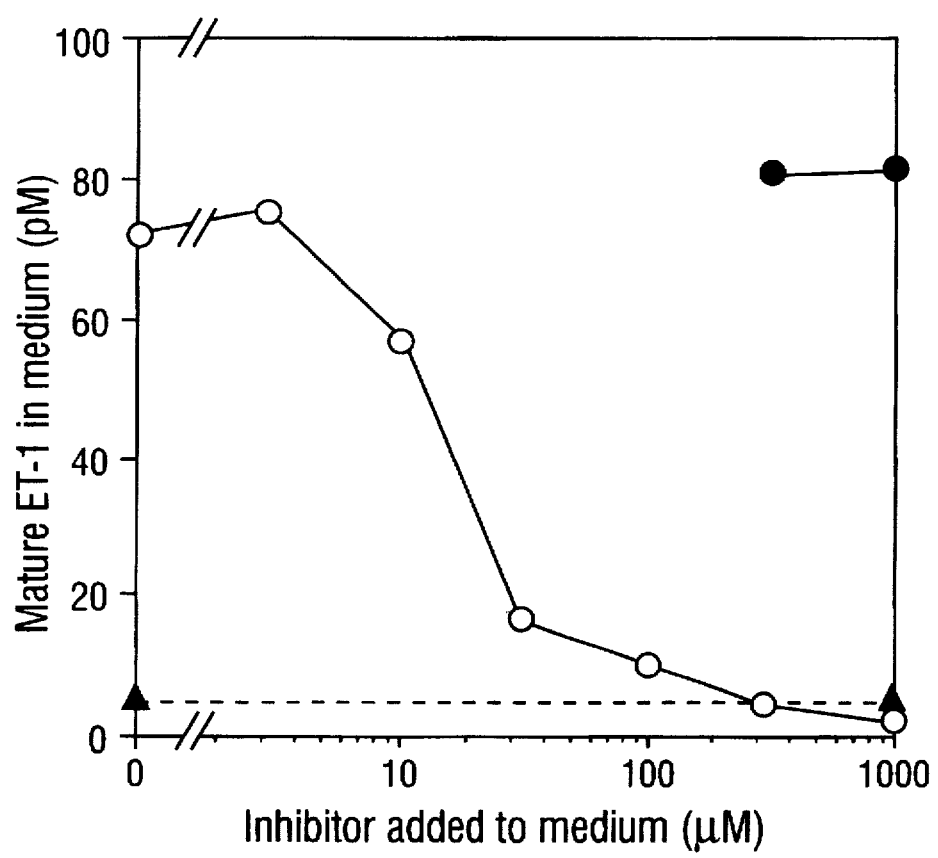
FIG. 2. Production of mature ET-1 by CHO/ECE-2 cells transiently transfected with preproET-1 cDNA: Cleavage of endogenously produced big ET-1. Doubly transfected cells were cultured for 12 h in the absence or presence of the designated concentrations of ECE inhibitors, and mature ET-1 in the conditioned medium was determined. Negative control studies with parental CHO cells are shown by dashed lines. Open circles, CHO/ECE-2 (Phosphoramidon); closed circles, CHO/ECE-2 (FR901533); closed triangles, CHO (Phosphoramidon). The activities are reported as pM of mature ET-1 in medium vs µM Inhibitor added to medium.

To examine whether ECE-2 can convert big ET-1 in a physiological context in transfected cells, a double-transfection assay was used (Xu et al., 1994). CHO/ECE-2 cells and untransfected CHO cells were transiently transfected in parallel with a preproET-1 construct, and mature ET-1 secreted from these cells into the medium was determined by EIA. As shown in FIG. 2, parental CHO cells transfected with preproET-1 cDNA did not secrete a significant amount of mature ET-1, consistent with the finding that CHO cells do not have detectable ECE activity. In contrast, CHO/ECE-2 cells transfected with the preproET-1 construct produced large amounts of mature peptide, indicating that ECE-2 cDNA conferred to these cells the ability to convert endogenously supplied big ET-1.

Figure 3:
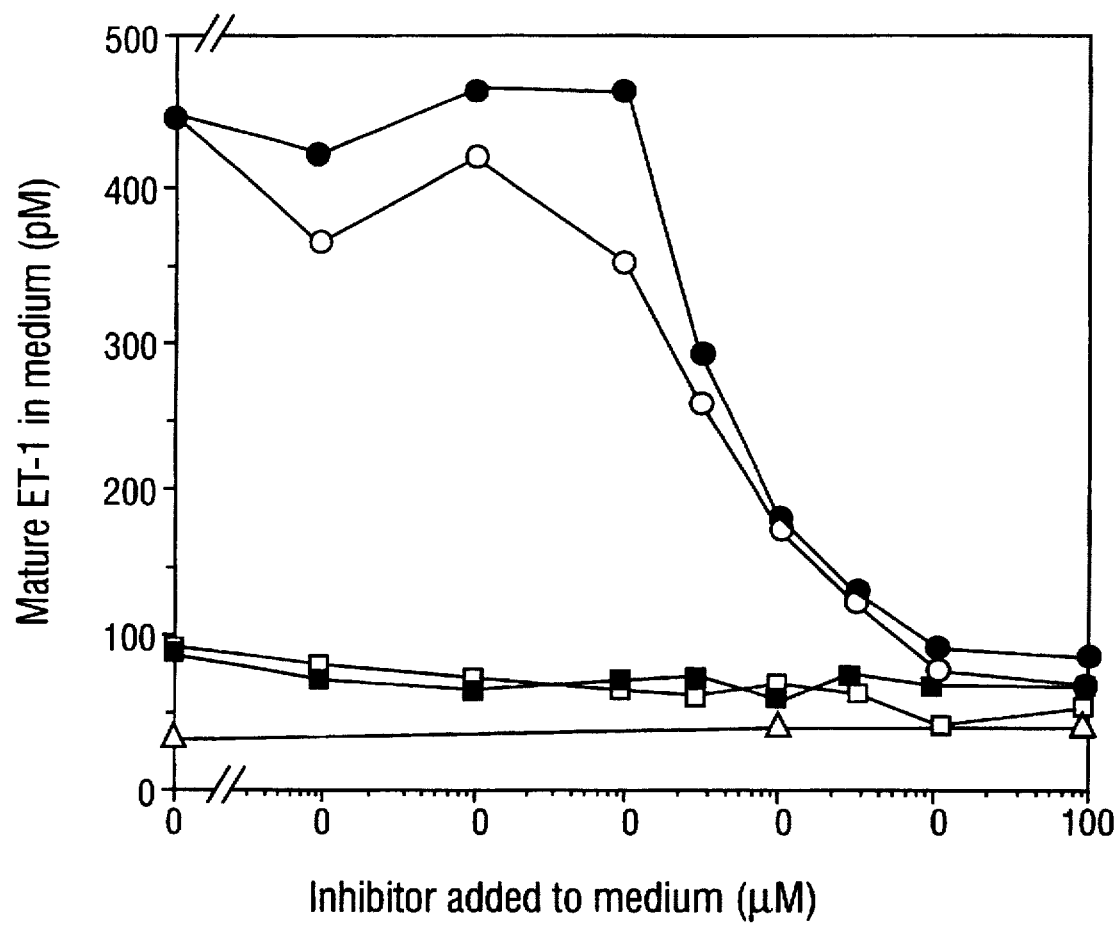
FIG. 3. Production of mature ET-1 by CHO/ECE-1-CHO/ preproET-1 and CHO/ECE-2-CHO/preproET-1 cocultures: Cleavage of exogenously supplied big ET-1. Cells are cocultured for 24 h in the absence or presence of the designated concentrations of phosphoramidon (phos) or FR901533 (FR), and mature ET-1 in the medium was determined. Negative control experiments were performed by coculturing parental CHO cells with CHO/preproET-1 cells. Open circles, CHO/ET-1+CHO/ECE-1 (Phos); closed circles, CHO/ET-1+CHO/ECE-1 (FR); open squares, CHO/ET-1+ CHO/ECE-2 (Phos); closed squares, CHO/ET-1+CHO/ ECE-2 (FR); open triangles, CHO/ET-1+CHO-K1 (Phos). Activity is reported as in FIG. 2.

Phosphoramidon has previously been shown to inhibit the secretion of mature ET-1 from cultured endothelial cells, with a concomitant increase of big ET-1 secretion (Sawamura et at., 1991). Also, phosphoramidon at high concentrations is capable of inhibiting the conversion of big ET-1 in cells doubly transfected with ECE-1 and preproET-1 cDNAs (Xu et al., 1994). FIG. 3 shows that phosphoramidon inhibits the production of mature ET-1 by the ECE-2-preproET-1 double transfected cells in a concentration dependent manner. The apparent $IC_{50}$ value in this live cell assay was about 20 µM, which is much higher than the $IC_{50}$ for the inhibitor determined in the test tube (4 nM, see FIG. 1B). Furthermore, FR901533, which efficiently inhibits the conversion of big ET-1 by ECE-2 in vitro, did not appreciably inhibit the conversion in the transfected cells when added to the medium at up to 1 mM. FR901533 is quite stable under culture conditions, and therefore the inability of the compound to inhibit the conversion is not due to degradation of FR901533 (Xu et al., 1994). These observations indicate that ECE-2 is processing big ET-1 inside the cells, where these inhibitors have limited access. The concentration of phosphoramidon required to inhibit big ET-1 conversion in the live CHO/ECE-2 cells was much lower than those in CHO/ECE-1 cells ($IC_{50}$>200 µM in a parallel assay). This presumably reflects the higher in vitro sensitivity of ECE-2 to phosphoramidon.

CHO/ECE-1 cells can also cleave exogenously added big ET-1, presumably owing to the location of some of the ECE-1 on the cell surface (Xu et al., 1994). Since ECE-2 has little activity at neutral pH, ECE-2 should be incapable of cleaving extracellular big ET-1 under normal culture conditions. This was tested by coculturing the stable transfectant CHO/preproET-1 cells with either CHO/ECE-1 or CHO/ECE-2 cells, and determining the amount of mature ET-1 in the medium. Consistent with previous findings, CHO/ECE-1 cells produced significant amounts of mature ET-1 in the coculture assay (FIG. 3). The production of mature peptide was readily inhibited by both phosphoramidon and FR901533 with $IC_{50}$ values (about 1 µM) similar to those seen in the in vitro assay, indicating that the conversion takes place on the cell surface. In contrast, only very small amounts of mature peptide were produced in the coculture of CHO/ECE-2 and CHO/preproET-1 cells. Moreover, mature peptide production was not inhibited by FR901533 at up to 100 µM or by phosphoramidon at up to 3 µM (FIG. 3). This is compatible with the notion either that ECE-2 is not expressed on the cell surface or that ECE-2 cannot convert exogenously supplied big ET-1 on the cell surface under normal tissue culture conditions, even if there is surface expression.

Reagents

Synthetic human big ET-1[1–38], big ET-2[1–38], big ET-3[1–41 amide], ET-1, ET-2 and ET-3 were obtained from American Peptides. Phosphoramidon, thiorphan, captopril, 1,10-phenanthroline, 4-amidino phenyl methyl sulphonyl fluoride (APMSF), p-chloro mercuri phenyl sulphonic acid (pCMS), N-ethylmaleimide (NEM), E-64, pepstatin A, and leupeptin were obtained from Sigma. FR901533 (WS79089B; 1,6,9,14-tetrahydroxy-3-(2-hydroxypropyl)-7-methoxy-8,13-dioxo-5,6,8,13-tetrahydro-benzo[α] naphthacene-2-carboxylate • Na) was a generous gift from Fujisawa Pharmaceutical Co., Ltd.

cDNA Cloning and Sequencing

A partial cDNA clone encoding ECE-2 was obtained by RT-PCR (Xu et al., 1994) against bovine adrenal cortex mRNA with highly degenerate primers based on a peptide microsequence from purified bovine ECE-1. Unamplified λgt10 bovine adrenal cortex and bovine endothelial cell cDNA libraries (Xu et al., 1994) were screened with the $^{32}$P-labeled RT-PCR product as probe. Nine and five positive plaques were identified in the adrenal cortex and endothelial libraries, respectively. The 5' end of the cDNA was cloned by 5'-RACE (Gibco/BRL) against bovine adrenal cortex poly(A)$^+$RNA. The first-strand cDNA was synthesized with SuperScript reverse transcriptase (Gibco/BRL) by using a specific primer ACAGGGGCTCACTCCA, SEQ ID NO:4 (corresponding to amino acids 134–139 of ECE-2). An oligo-dC anchor was added to the 3' end of the first-strand cDNA with terminal deoxynucleotidyl transferase. The first round of PCR was performed as recommended by the manufacturer with a specific 3' primer CTCCAGGATTTTTCCAGCCACTCGA, SEQ ID NO:5 (amino acids 122–130) and a 5' anchor primer. The product of this PCR reaction was subjected to the second amplification by using a nested specific 3' primer GGCCTCTGTGAGGCAAGTGCTATG, SEQ ID NO:6 (amino acids 113–120). The products from three independent 5'-RACE reactions were separately subcloned into pCR II plasmid (Invitrogen) and sequenced. For nucleotide sequencing, overlapping restriction fragments of cDNA were subcloned in pBlueScript plasmid vector (Stratagene), and double-strand plasmid DNA were PCR-sequenced by an Applied Biosystems model 373A DNA Sequenator. Both strands of cDNA were sequenced at least twice. Some subclones were manually sequenced using the Sequenase kit (USB).

Northern Blotting

RNA was extracted from bovine tissues by the LiCl/urea method (Inoue et al., 1989). Total RNA (10 µg) was separated in a formaldehyde/1.1% agarose gel, transferred to a nylon membrane, and prehybridized and hybridized in QuickHyb solution (Stratagene) as recommended by the manufacturer. A 0.3-kb Eco47III-XhoI fragment of the bovine ECE-2 cDNA, which encodes amino acids 198–283 and does not cross-hybridize with the ECE-1 mRNA, was random-primed, $^{32}$P-labeled and used as probe. The membranes were washed finally in 0.1×SSC/0.1% SDS at 60° C., and exposed to an X-ray film for 24 h (ECE-2) and for 90 min (β-actin) at −80° C. with an intensifying screen.

Antibodies and Immunoblotting

Antibodies directed against ECE-1 and ECE-2 were each produced by immunizing rabbits with synthetic peptides, CPPGSPMNPHHKCEVW, SEQ ID NO:7 and CPVGSPMNSGQLCEVW, SEQ ID NO:3, corresponding to the C-terminal 16 amino acids of bovine ECE-1 and ECE-2, respectively. Rabbits were immunized with keyhole limpet hemocyanin-coupled peptides in complete adjuvant, and the antisera were prepared. Immunoblot analysis was performed with horseradish peroxidase-conjugated anti-rabbit IgG by using the ECL detection kit (Amersham) as recommended by the manufacturer.

Cell Culture and Transfection

CHO-K1 cells were cultured as described (Xu et al., 1994). Since many batches of tissue culture-grade trypsin preparations contained high levels of metalloprotease contaminants with an ECE-like activity, a highly purified crystallized preparation of trypsin (Sigma, Catalog No. T7418) was dissolved in phosphate-buffered saline at 0.013% (w/v) and used for all trypsinization procedures. The coding region of bovine ECE-2 cDNA was subcloned into pME18Sf-expression vector (Sakamoto et al., 1993). Stable transfection of CHO cells and isolation of the transfectant clones, as well as transient transfection of human preproET-1 cDNA was performed as described (Xu et al., 1994). Twelve hours after the transient transfection, cells were refed with fresh medium with or without ECE inhibitors. The medium was conditioned for an additional 12 h and directly subjected to enzyme immunoassay (EIA) for mature ET-1 (Suzuki et al., 1989).

Purification of ECE

Bovine adrenal glands were obtained at a local slaughter house, immediately immersed in ice-cold Dulbecco's phosphate buffered saline (PBS), and brought to the laboratory within 2 hours. All subsequent procedures were performed at 4° C. Adrenal cortices were carefully separated from the medulla and connective tissue. The cortices (≈80 per batch) were minced by a food processor and immediately homogenized in 4×volume of buffer A (20 mM Tris-HCl (pH 7.4)/20 µM pepstatin A/1 mM PMSF/1 mM NEM) containing 250 mM sucrose by a Polytron homogenizer at 10,000 r.p.m. for 3×15 sec. The homogenate was centrifuged at 1,000×g for 10 min, and the resulting supernatant was further centrifuged at 100,000×g for 60 min. The pellet was resuspended in 5×volume of buffer A by a Teflon homogenizer, and centrifuged again at 100,000×g for 60 min. The crude membrane pellet was solubilized at 10–20 mg protein/ml in buffer A containing 2.5% $C_{12}E_{10}$ for 30 min. The mixture was centrifuged at 100,000×g for 60 min, and the supernatant was saved as solubilized membrane.

The purification scheme was partly based on a published procedure (Takahashi et al., 1993). Solubilized membrane was applied to a DEAE column (DEAE Toyopearl 650S, 2.6×20 cm; Toso-Haas) preequilibrated with 20 mM Tris-HCl (pH 7.4) containing 0.1% $C_{12}E_{10}$. The column was eluted at a flow rate of 3 ml/min with a linear gradient of 0–0.5M NaCl in 400 ml of the same buffer. The active fractions were pooled and loaded to a wheat-germ agglutinin (WGA) agarose column (2.6×9.5 cm; Seikagaku USA) equilibrated with 20 mM Tris-HCl (pH 7.4)/0.15M NaCl/ 0.015% $C_{12}E_{10}$. The column was washed at a flow rate of 0.5 ml/min with 100 ml of the same buffer, and eluted with the same buffer containing 50 mg/ml N-acetylglucosamine. The active fractions were applied at a flow rate of 0.5 ml/min to a zinc chelating column (Chelating Sepharose FF, 1.6×8.5 cm; Pharmacia) preequilibrated with 20 mM Tris-HCl (pH 7.4)/0.15M NaCl/0.015% $C_{12}E_{10}$. The flow-through fractions containing ECE activity from the zinc chelating column were loaded at a flow rate of 0.5 ml/min to a Blue-B dye agarose column (1.6×10 cm; Amicon) equilibrated with 20 mM Tris-HCl (pH 7.4)/1M NaCl/0.015% $C_{12}E_{10}$. After washing the column with 100 ml of the same buffer, the column was connected to a WGA-agarose column (1.6×6.5 cm) and then eluted at a flow rate of 0.2 ml/min with 150 ml of 3M NaCl/1M urea/20 mM Tris-HCl (pH 7.4)/0.015% $C_{12}E_{10}$. The WGA column was disconnected and equilibrated at a flow rate of 0.2 ml/min with 140 ml of 20 mM Tris-HCl (pH 7.4)/0.15M NaCl/25 mM n-octylglucoside. The column was eluted with 40 ml of the same buffer containing 50 mg/ml N-acetylglucosamine at a flow rate of 0.2 ml/min. The active fractions were pooled, diluted 2 fold and applied to a Mono Q HR 5/5 column (Pharmacia) equilibrated with 20 mM BisTris-HCl (pH 7.0)/25 mM n-octylglucoside. The column was eluted at a flow rate of 1 ml/min with a linear gradient of 0–0.5M NaCl in 30 ml of the same buffer.

ECE Assays

Solubilized crude membranes were prepared in parallel from CHO/ECE-2 and CHO/ECE-1 cells as described (Xu et al., 1994). For protease inhibitor studies, membranes were prepared without protease inhibitors. Standard reaction mixtures for the ECE-2 assay (50 µl) contained 0.1M 2-[N-morpholino]ethanesulfonic acid (MES) buffer (pH 5.5), 0.5M NaCl, 0.1 µM human big ET-1 and an enzyme fraction. ECE-1 assay reactions contained 0.1M phosphate buffer (pH 6.8) instead of the MES buffer. For the pH profiling and isopeptide selectivity studies, the buffer solution (0.1M) or the substrate (0.1 µM) was substituted as designated. For the inhibitor studies, the reactions were preincubated at 37° C. with protease inhibitor or vehicle for 15 min. Reactions were started by the addition of substrate, and incubated at 37° C. for 30 min in siliconized 0.5-ml microcentrifuge tubes. Enzyme reactions were terminated by adding 50 µl of 5 mM EDTA. The mixture was then directly assayed for mature ET-1 as described (Suzuki et al., 1989). Duplicate assay wells were used for each enzyme reaction. For big ET-2 and big ET-3 conversion assays, mature ET-1 EIA (which fully cross-reacts with mature ET-2) and mature ET-3 EIA were used with human ET-2 and ET-3 as standards, respectively (Matsumoto et al., 1989). Protein concentrations were determined by the Bradford method (Bio-Rad) using IgG as standard.

EXAMPLE 2

| ECE-2 Amino Acid Sequence | | | | | |
|---|---|---|---|---|---|
| MRARYAHVPT | LRWETMDVRA | LGFPSGSFDV | VLEKGTLDAL | LTGEQDPWTV | SSEGVHTVDQ |
| VLNEAGFRKR | TSRLLGLHTQ | LELVLAGVSL | LLAALLLGCL | VALGVQYHRD | PSHSTCLTEA |
| CIRVAGKILE | SLDRGVSPCE | DFYQFSCGGW | IRRNPLPDGR | SRWNNSNSLW | DQNQAILKHL |
| LENTTFNSSS | EAERKTQRFY | LSCLQVERIE | ELGAHALRDL | IDKIGGWNVT | GPWDQDNFME |
| VLKAVAGTYR | ATPFFTVYVS | ADSKSSNSNI | IQVDQSGLFL | PSRDYYLNRT | ANEKVLTAYL |
| DYMEELGMLL | GGQPTSTREQ | MRQVLELEIQ | LANITVPQDQ | RRDEEKIYHK | MSIAELQALA |
| PSMDWLEFLS | FLLSPLELGD | SEPVVVYGTD | YLQQVSELIN | RTEPSVLNNY | LIWNLVQKTT |
| SSLDHRFESA | QEKLLETLYG | TKKSCTPRWQ | TCISNTDDAL | GFALGSLFVK | ATFDRQSKEI |
| AEGMISEIRV | AFEEALGHLV | WMDEKTRQAA | KEKADAIYDM | IGFPDFILEP | KELDDVYDGY |
| EVSEDSFFQN | MLNLYNFSAK | VMADQLRKPP | SRDQWSMTPQ | TVNAYYLPTK | NEIVFPAGIL |
| QAPFYTCNHP | QALNFGGIGV | VMGHELTHAF | DDQGREYDKE | GNLRPWWQNE | SLAAFRNHTA |
| CIEEQYSQYQ | VNGEKLNGRQ | TLGENIADNG | GLKAAYNAYK | AWLRKHGEEQ | QLPAVGLTNH |
| QLFFVGFAQV | WCSVRTPESS | HEGLVTDPHS | PARFRVLGTL | SNSRDFLRHF | GCPVGSPMNS |
| GQLCEVW, SEQ ID NO: 2. | | | | | |

EXAMPLE 3

| ECE-2 cDNA Sequence | | | | | |
|---|---|---|---|---|---|
| ttggaccgta | tcctcgtgct | aggctgtgga | aacagtgccc | tgagctacga | gctattgctt |
| ggggggcttc | cctgatgtga | ccagtgtgga | ctactcatca | gtagtggtgg | ctgccatgag |
| ggctcggtat | gcccacgtgc | ccacgctgcg | atgggagacc | atggatgtgc | gggcactggg |
| cttccctagt | ggctctttcg | acgtggtgct | tgagaagggc | acactggatg | ccctgttgac |
| tggtgaacag | gatccctgga | ctgtgtcctc | tgaaggtgtc | cacactgtgg | accaggtgct |
| aaatgaggcg | ggattccgga | agaggaccag | tcgcctcttg | gggttgcaca | cccagctgga |
| gctggtcttg | gctggtgtct | ctctactgct | ggctgccctg | cttctgggtt | gcttggtggc |
| cctgggggta | cagtaccaca | gagacccatc | ccatagcact | tgcctcacag | aggcctgcat |
| tcgagtggct | ggaaaaatcc | tggagtccct | ggaccgtgga | gtgagcccct | gtgaggactt |

ECE-2 cDNA Sequence

| | | | | | |
|---|---|---|---|---|---|
| ctatcagttc | tcctgcggag | gctggattcg | gagaaaccct | ctacctgatg | ggcgttctcg |
| ctggaacaac | tccaacagtc | tctgggacca | gaatcaagcc | atcctgaagc | acctgcttga |
| aaacaccacc | ttcaactcca | gcagtgaagc | tgaacggaag | acgcagcgct | tctacctctc |
| ctgcttacag | gtgggagcgca | tcgaggagct | gggtgcccac | gcactgcgag | acctcattga |
| caagattggt | ggctggaacg | ttacggggcc | ctgggaccag | gacaacttca | tggaggtgct |
| gaaggcagtg | gcagggacgt | atagggccac | cccctctt | actgtctacg | tcagtgccga |
| ctctaagagt | tccaacagca | atattatcca | ggtggaccag | tctgggctct | ttctaccctc |
| tcgagattac | tacctaaaca | ggaccgccaa | tgagaaagtg | cttactgcct | acctggacta |
| catggaggag | ctggggatgc | tgctgggcgg | acagccaacc | tccactcggg | agcagatgcg |
| gcaggtgctg | gagctggaga | tacaactggc | caacatcacg | gtgcccagg | accagcggcg |
| ggatgaggag | aagatctacc | acaagatgag | catcgcggag | ctgcaggcc | tggcaccctc |
| catggattgg | ctggagtttc | tgtccttctt | gctgtcaccg | ctggagctgg | gtgattctga |
| gcctgtggtg | gtgtatggga | cggattattt | gcagcaggtg | tcggaactca | tcaaccgcac |
| agagccaagt | gtcctgaaca | attatctgat | ctggaacctg | gtacagaaga | caacttcaag |
| cctggaccac | cgctttgagt | ctgcacaaga | aaagctgctg | gagaccctct | atggcaccaa |
| gaagtcctgt | acaccgaggt | ggcagacctg | catctccaac | accgacgatg | ctcttggctt |
| tgctctgggc | tccctctttg | tgaaggccac | atttgaccgg | cagagcaagg | aaattgcaga |
| gggggatgatc | agcgagatcc | gagtcgcctt | tgaggaggct | ctgggacact | tggtttggat |
| ggacgagaag | acccgccagg | cagccaagga | gaaagcagat | gccatctatg | atatgattgg |
| ttcccggac | ttcatcctgg | agcccaaaga | gctggatgat | gtttatgatg | ggtatgaagt |
| atctgaagat | tccttcttcc | agaacatgtt | gaatttgtac | aacttctctg | ctaaagtgat |
| ggctgaccag | ctccgcaagc | ctcctagccg | agaccagtgg | agcatgaccc | cgcagacagt |
| gaacgcctac | taccttccaa | ccaagaatga | aatcgtcttc | cctgctggca | tcctgcaggc |
| cccttctac | acttgcaacc | accccccaggc | cctgaacttc | ggtggcatcg | gtgtggtgat |
| gggccacgag | ttgacacatg | cctttgatga | ccaagggcgc | gagtatgaca | aggaagggaa |
| tctgcggccg | tggtggcaga | atgagtcgtt | ggcagccttc | cggaaccaca | cggcctgcat |
| agaggagcag | tacagccagt | accaggtcaa | cggggagaag | ctcaacgggc | gccagacact |
| gggggagaac | attgccgaca | atgggggct | taaggctgcc | tacaacgctt | acaaagcatg |
| gctaagaaag | catgggagg | agcagcagct | gccagctgtg | ggactcacca | accaccagct |
| cttctttgtg | ggatttgccc | aggtgtggtg | ctcggtccgc | acacccgaga | gctctcacga |
| gggggctggtg | accgacccc | acagccctgc | ccgcttccgt | gtgctgggca | ctctctccaa |
| ctcccgtgac | ttcctgcggc | acttcggctg | ccctgtcggc | tcccccatga | actcagggca |
| gctttgtgag | gtgtggtaga | cctgggttgg | gagagaaatg | gccagctcgg | ttgccggagc |
| ctggggtatc | ttgcccagcc | aggctctctg | ctctgggggt | gatggaaggc | acatgccagc |
| tgggctgtgt | cctgcccctc | cacaccatag | gtgtgacatg | agtcctagtc | cctcctcggc |
| ctccacatcg | tgcctctgct | ttgggggtgc | ccctgcctcc | agcagagtcc | ccaccattca |
| ctgtgatgtt | ctttgccacc | ctgcctggag | gaggcctggg | caggggccac | cagctcccac |
| aagaaggggt | ccacctcttt | aggtccccag | ctcagtgggt | ttggtggoca | cagggcctat |
| tgtgcctgct | gaccacgcag | ggcccgacag | atgtgcctcc | cacacatctc | cccaaggctt |
| actcactgct | cccttgggca | tagacagagc | tccttttcagc | cctgccccca | gtggcgacct |
| ttattccatg | ttcctcatgc | cactgctcct | aatactgctg | ccagccctct | ctgacggacc |
| ccctgtgctg | agctcttagt | ggaagtccaa | cagcctttac | aaaccttcct | gttgcctccc |
| agggtccctg | ggctcagcgg | ggatgtgtgt | acatgtcagg | gatgctaggc | cctgcatctt |
| ggggttacaa | gtcttagggg | gtgactgatt | ctccctggac | caagcaggaa | agcagataga |
| gtaggaagag | tgaaggatag | agtctatttt | tacaggaaag | ggtgagggga | gggagtggtc |
| tggccctgg | aggaccctgt | gccaataaat | agacacgcat | cagtcaaaaa | a, SEQ ID |
| NO: 1. | | | | | |

EXAMPLE 4

Use of the cDNA to Isolate the Full Length Gene

The sequence of the cloned cDNA gene encoding ECE-2 is useful as a primer or a probe to isolate the full length gene encoding the ECE-2 protein. The techniques to accomplish the isolation of the full length gene are well known in the art. For example, a genomic library, from bovine adrenal cortex for example, is constructed by well known techniques and screened with the cDNA sequence, or a portion of the sequence that is amplified by the polymerase chain reaction, for example. The library would be separated, for example by polyacrylamide gel electrophoresis, or agarose gel electrophoresis and then transferred to a filter such as a nitrocellulose filter. The cDNA may be labeled with $^{32}$P by enzymatic labelling with polynucleotide kinase, for example, or labelled nucleotides may be used during amplification to create a labeled probe. Alternatively, the probe could be labeled with a fluorescent marker such as biotin or any fluorophore. Such labelling techniques are well known in the art.

The labeled probe would then be hybridized to the denatured DNA clones on the filter and washed under increasingly stringent conditions, incrementally higher temperatures for example, until the positive clones can be identified by autoradiography or by fluorescence. These positive clones would then be rescreened and sequenced to determine the full gene sequence encoding the ECE-2 protein.

The full protein could then be expressed in an *E. coli* strain, for example, or a eukaryotic host cell and used for further analysis. It is understood that the protein could also be truncated or altered by site directed mutagenesis, for example and that such altered proteins or partial sequences would also fall within the scope of the present invention.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahn, K., Beningo, K., Olds, G., and Hupe, D. (1992) *Proc. Natl. Acad. Sci. USA* 89, 8606–8610

Anderson, R. G. W., and Orci, L. (1988) *J. Cell. Biol.* 106, 539–543

Arai, H., Hori, S., Aramori, I., Ohkubo, H., and Nakanishi, S. (1990) *Nature* 348, 730–732

Arai, K., Ashikawa, N., Nakakita, Y., Matsuura, A., Ashizawa, N and Munekata, M. (1993) *Biosci. Biotech. Biochem*, 57, 1944–1945

Baynash, A. G., Hosoda, K., Giaid, A., Richardson, J. A., Emoto, N., Hammer, R. E., and Yanagisawa, M. (1994) *Cell* 79, 1277–1285

Clozel, M., Breu, V., Burri, K., Cassal, J.-M., Fischli, W., Gray, G. A., Hirth, G., Loftier, B.-M., Muller, M., Neldhart, W., and Ramuz, H. (1993) *Nature* 365, 759–761

Douglas, S. A., Meek, T. D., and Ohlstein, E. H. (1994) *Trends Pharmacol. Sci.* 15, 313–316

Giaid, A., Yanagisawa, M., Langleben, D., Michel, R. P., Levy, R., Shennib, H., Kimura, S., Masaki, T., Duguid, W. P., and Stewart, D. J. (1993) *N. Engl. J. Med.* 328, 1732–1740

Hosoda, K., Hammer, R. E., Richardson, J. A., Greenstein Baynash, A., Cheung, J. C., Giaid, A., and Yanagisawa, M. (1994) *Cell* 79, 1267–1276

Inoue, A., Yanagisawa, M., Takuwa, Y., Mitsui, Y., Kobayashi, M., and Masaki, T. (1989) *J. Biol. Chem.* 264, 14954–14959

Inoue, A., Yanagisawa, M., Kimura, S., Kasuya, Y., Miyauchi, T., Goto, K., and Masaki, T. (1989) *Proc. Natl. Acad. Sci. USA* 86, 2863–2867

Kurihara, Y., Kurihara, H., Suzuki, H., Kodama, T., Maemura, K., Nagai, R., Oda, H., Kuwaki, T., Cao, W., Kamada, N., Jishage, K., Ouchi, Y., Azuma, S., Toyoda, Y., Ishikawa, T., Kumada, M., and Yazaki, Y. (1994) *Nature* 368, 703–710

Lee, S., Zambas, E. D., Marsh, W. L., and Redman, C. M. (1991) *Proc. Natl. Acad. Sci. USA* 88, 6353–6357

Malfroy, B., Kuang, W. J., Seedburg, P. H., Mason, A. J., and Schofield, P. R. (1988) *FEBS Lett.* 229, 206–210

Matsumoto, H., Suzuki, N., Onda, H., and Fujino, M. (1989) *Biochem. Biophys. Res. Comm.* 164, 74–80

Ohlstein, E. H., Nambi, P., Douglas, S. A., Edwards, R. M., Gellai, M., Lago, A., Leber, J. D., Cousins, R. D., Gao, A., Frazee, J. S., Peishoff, C. E., Bean, J. W., Eggleston, D. S., Elshourbagy, N. A., Kumar, C., Lee, J. A., Brooks, D. P., Weinstock, J., Feuerstein, G., Poste, G., et al. (1994) *Proc. Natl. Acad. Sci. USA* 91, 8052–8056

Okada, K., Arai, Y., Hata, M., Matsuyama, K., and Yano, M. (1993) *Eur. J. Biochem.* 218, 493–498

Opgenorth, T. J., Wu-Wong, J. R., and Shiosaki, K. (1992) *FASEB J.* 6, 2653–2659

Rawlings, N. D., and Barrett, A. J. (1993) *Biochem. J.* 290, 205–218

Roques, B. P., Noble, F., Dauge, V., Fournie-Zaluski, M.-C., and Beaumont, A. (1993) *Pharmacol. Rev.* 45, 87–146

Rubanyi, G. M., and Polokoff, M. A. (1994) *Pharmacol. Rev.* 46, 325–415

Sakamoto, A., Yanagisawa, M., Sawamura, T., Enoki, T., Ohtani, T., Sakurai, T., Nakao, K., Toyo-oka, T., and Masaki, T. (1993) *J. Biol. Chem.* 268, 8547–8553

Sakurai, T., Yanagisawa, M., Takuwa, Y., Miyazaki, H., Kimura, S., Goto, K., and Masaki, T. (1990) *Nature* 348, 732–735 7. Bax, W. A., and Saxena, P. R. (1994) *Trands Pharmacol. Sci.* 15, 379–386

Sawamura, T., Kasuya, Y., Matsushita, Y., Suzuki, N., Shinmi, O., Kishi, N., Sugita, Y., Yanagisawa, M., Goto, K., Masaki, T., and Kimura, S. (1991) *Biochem. Biophys. Res. Comm.* 174, 779–784

Seidah, N. G., Day, R., Marcinkiewicz, M., and Chretien, M. (1993) *Ann. New York Acad. Sci.* 680, 135–146

Shimada, K., Takahashi, M., and Tanzawa, K. (1994) *J. Biol. Chem.* 269, 18275–18278

Suzuki, N., Matsumoto, H., Kitada, C., Masaki, T., and Fujino, M. (1989) *J. Immunol. Meth.* 118, 245–250

Takahashi, M., Matsushita, Y., Iijima, Y., and Tanzawa, K. (1993) *J. Biol. Chem.* 268, 21395–21398

Wilhelm, S. M., Shao, Z.-H., Housley, T. J., Seperack, P. K., Baumann, A. P., Gunja-Smith, Z., and Woessner, J., J. F. (1993) *J. Biol. Chem.* 268, 21906–21913

Xu, D., Emoto, N., Giaid, A., Slaughter, C., Kaw, S., deWit, D., and Yanagisawa, M. (1994) *Cell* 78, 473–485

Yanagisawa, M. (1994) *Circulation* 89, 1320–1322

Yanagisawa, M., Kurihara, H., Kimura, S., Tomobe, Y., Kobayashi, M., Mitsui, Y., Yazaki, Y., Goto, K., and Masaki, T. (1988) *Nature* 332, 411–415

---

What is claimed is:

1. A composition comprising a partially purified endothelin converting enzyme-2 (ECE-2) polypeptide, having an activity of at least about 275 fmol/30 min/20 μg at pH 5.6–5.6.

2. The composition of claim 1, wherein said partially purified endothelin converting enzyme-2 (ECE-2) polypeptide comprises a contiguous amino acid sequence consisting of SEQ ID NO:2.

3. The composition of claim 1, wherein said partially purified endothelin converting enzyme-2 (ECE-2) polypeptide is a recombinant polypeptide.

4. The composition of claim 2, wherein said amino acid sequence is encoded by a nucleic acid sequence including the coding region of SEQ ID NO:1.

5. The composition of claim 3, wherein said recombinant polypeptide is expressed in a chinese hamster ovary cell.

6. An antigenic composition comprising the C-terminal region of endothelin converting enzyme-2.

7. The antigenic composition of claim 6, wherein said terminal region comprises the amino acid sequence, CPVGSPMNSGQLCEVW, SEQ ID NO:3.

* * * * *

UNITED STATES PATENT AND TRADEMARK OFFICE
CERTIFICATE OF CORRECTION

PATENT NO.   :   5,736,376

DATED        :   April 7, 1998

INVENTOR(S)  :   Masashi Yanagisawa

It is certified that error appears in the above-identified patent and that said Letters Patent is hereby corrected as shown below:

In claim 1, column 43, line 53, please delete "5.6-5.6.", and insert the following therefor: -- 5.5-5.6. --.

Signed and Sealed this

Twenty-sixth Day of January, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 3291 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 116..2476

( x i ) SEQUENCE DESCRIPTION: SEQ ID NO:1:

```
TTGGACCGTA TCCTCGTGCT AGGCTGTGGA AACAGTGCCC TGAGCTACGA GCTATTCTT         60
```

-continued

| | | | | | | | | | | | | | | | | |
|---|---|---|---|---|---|---|---|---|---|---|---|---|---|---|---|---|
| GGGGGGCTTC | CCTGATGTGA | CCAGTGTGGA | CTACTCATCA | GTAGTGGTGG | CTGCC | ATG Met 1 | | | | | | | | | | 118 |

| AGG | GCT | CGG | TAT | GCC | CAC | GTG | CCC | ACG | CTG | CGA | TGG | GAG | ACC | ATG | GAT | 166 |
|---|---|---|---|---|---|---|---|---|---|---|---|---|---|---|---|---|
| Arg | Ala | Arg | Tyr 5 | Ala | His | Val | Pro | Thr 10 | Leu | Arg | Trp | Glu | Thr 15 | Met | Asp | |

| GTG | CGG | GCA | CTG | GGC | TTC | CCT | AGT | GGC | TCT | TTC | GAC | GTG | GTG | CTT | GAG | 214 |
|---|---|---|---|---|---|---|---|---|---|---|---|---|---|---|---|---|
| Val | Arg | Ala 20 | Leu | Gly | Phe | Pro | Ser 25 | Gly | Ser | Phe | Asp | Val 30 | Val | Leu | Glu | |

| AAG | GGC | ACA | CTG | GAT | GCC | CTG | TTG | ACT | GGT | GAA | CAG | GAT | CCC | TGG | ACT | 262 |
|---|---|---|---|---|---|---|---|---|---|---|---|---|---|---|---|---|
| Lys | Gly | Thr 35 | Leu | Asp | Ala | Leu | Leu 40 | Thr | Gly | Glu | Gln | Asp 45 | Pro | Trp | Thr | |

| GTG | TCC | TCT | GAA | GGT | GTC | CAC | ACT | GTG | GAC | CAG | GTG | CTA | AAT | GAG | GCG | 310 |
|---|---|---|---|---|---|---|---|---|---|---|---|---|---|---|---|---|
| Val 50 | Ser | Ser | Glu | Gly | Val 55 | His | Thr | Val | Asp | Gln 60 | Val | Leu | Asn | Glu | Ala 65 | |

| GGA | TTC | CGG | AAG | AGG | ACC | AGT | CGC | CTC | TTG | GGG | TTG | CAC | ACC | CAG | CTG | 358 |
|---|---|---|---|---|---|---|---|---|---|---|---|---|---|---|---|---|
| Gly | Phe | Arg | Lys | Arg 70 | Thr | Ser | Arg | Leu | Leu 75 | Gly | Leu | His | Thr | Gln 80 | Leu | |

| GAG | CTG | GTC | TTG | GCT | GGT | GTC | TCT | CTA | CTG | CTG | GCT | GCC | CTG | CTT | CTG | 406 |
|---|---|---|---|---|---|---|---|---|---|---|---|---|---|---|---|---|
| Glu | Leu | Val | Leu 85 | Ala | Gly | Val | Ser | Leu 90 | Leu | Leu | Ala | Ala | Leu 95 | Leu | Leu | |

| GGT | TGC | TTG | GTG | GCC | CTG | GGG | GTC | CAG | TAC | CAC | AGA | GAC | CCA | TCC | CAT | 454 |
|---|---|---|---|---|---|---|---|---|---|---|---|---|---|---|---|---|
| Gly | Cys | Leu 100 | Val | Ala | Leu | Gly | Val 105 | Gln | Tyr | His | Arg | Asp 110 | Pro | Ser | His | |

| AGC | ACT | TGC | CTC | ACA | GAG | GCC | TGC | ATT | CGA | GTG | GCT | GGA | AAA | ATC | CTG | 502 |
|---|---|---|---|---|---|---|---|---|---|---|---|---|---|---|---|---|
| Ser | Thr 115 | Cys | Leu | Thr | Glu | Ala 120 | Cys | Ile | Arg | Val | Ala 125 | Gly | Lys | Ile | Leu | |

| GAG | TCC | CTG | GAC | CGT | GGA | GTG | AGC | CCC | TGT | GAG | GAC | TTC | TAT | CAG | TTC | 550 |
|---|---|---|---|---|---|---|---|---|---|---|---|---|---|---|---|---|
| Glu 130 | Ser | Leu | Asp | Arg | Gly 135 | Val | Ser | Pro | Cys | Glu 140 | Asp | Phe | Tyr | Gln | Phe 145 | |

| TCC | TGC | GGA | GGC | TGG | ATT | CGG | AGA | AAC | CCT | CTA | CCT | GAT | GGG | CGT | TCT | 598 |
|---|---|---|---|---|---|---|---|---|---|---|---|---|---|---|---|---|
| Ser | Cys | Gly | Gly | Trp 150 | Ile | Arg | Arg | Asn | Pro 155 | Leu | Pro | Asp | Gly | Arg 160 | Ser | |

| CGC | TGG | AAC | AAC | TCC | AAC | AGT | CTC | TGG | GAC | CAG | AAT | CAA | GCC | ATC | CTG | 646 |
|---|---|---|---|---|---|---|---|---|---|---|---|---|---|---|---|---|
| Arg | Trp | Asn | Asn 165 | Ser | Asn | Ser | Leu | Trp 170 | Asp | Gln | Asn | Gln | Ala 175 | Ile | Leu | |

| AAG | CAC | CTG | CTT | GAA | AAC | ACC | ACC | TTC | AAC | TCC | AGC | AGT | GAA | GCT | GAA | 694 |
|---|---|---|---|---|---|---|---|---|---|---|---|---|---|---|---|---|
| Lys | His | Leu 180 | Leu | Glu | Asn | Thr | Thr 185 | Phe | Asn | Ser | Ser | Ser 190 | Glu | Ala | Glu | |

| CGG | AAG | ACG | CAG | CGC | TTC | TAC | CTC | TCC | TGC | TTA | CAG | GTG | GAG | CGC | ATC | 742 |
|---|---|---|---|---|---|---|---|---|---|---|---|---|---|---|---|---|
| Arg | Lys 195 | Thr | Gln | Arg | Phe | Tyr 200 | Leu | Ser | Cys | Leu | Gln 205 | Val | Glu | Arg | Ile | |

| GAG | GAG | CTG | GGT | GCC | CAC | GCA | CTG | CGA | GAC | CTC | ATT | GAC | AAG | ATT | GGT | 790 |
|---|---|---|---|---|---|---|---|---|---|---|---|---|---|---|---|---|
| Glu 210 | Glu | Leu | Gly | Ala | His 215 | Ala | Leu | Arg | Asp | Leu 220 | Ile | Asp | Lys | Ile | Gly 225 | |

| GGC | TGG | AAC | GTT | ACG | GGG | CCC | TGG | GAC | CAG | GAC | AAC | TTC | ATG | GAG | GTG | 838 |
|---|---|---|---|---|---|---|---|---|---|---|---|---|---|---|---|---|
| Gly | Trp | Asn | Val | Thr 230 | Gly | Pro | Trp | Asp | Gln 235 | Asp | Asn | Phe | Met | Glu 240 | Val | |

| CTG | AAG | GCA | GTG | GCA | GGG | ACG | TAT | AGG | GCC | ACC | CCC | TTC | TTT | ACT | GTC | 886 |
|---|---|---|---|---|---|---|---|---|---|---|---|---|---|---|---|---|
| Leu | Lys | Ala | Val 245 | Ala | Gly | Thr | Tyr | Arg 250 | Ala | Thr | Pro | Phe | Phe 255 | Thr | Val | |

| TAC | GTC | AGT | GCC | GAC | TCT | AAG | AGT | TCC | AAC | AGC | AAT | ATT | ATC | CAG | GTG | 934 |
|---|---|---|---|---|---|---|---|---|---|---|---|---|---|---|---|---|
| Tyr | Val | Ser 260 | Ala | Asp | Ser | Lys | Ser 265 | Ser | Asn | Ser | Asn | Ile 270 | Ile | Gln | Val | |

| GAC | CAG | TCT | GGG | CTC | TTT | CTA | CCC | TCT | CGA | GAT | TAC | TAC | CTA | AAC | AGG | 982 |
|---|---|---|---|---|---|---|---|---|---|---|---|---|---|---|---|---|
| Asp | Gln | Ser 275 | Gly | Leu | Phe | Leu | Pro 280 | Ser | Arg | Asp | Tyr | Tyr 285 | Leu | Asn | Arg | |

| ACC | GCC | AAT | GAG | AAA | GTG | CTT | ACT | GCC | TAC | CTG | GAC | TAC | ATG | GAG | GAG | 1030 |
|---|---|---|---|---|---|---|---|---|---|---|---|---|---|---|---|---|
| Thr | Ala | Asn | Glu 290 | Lys | Val | Leu | Thr | Ala 295 | Tyr | Leu | Asp | Tyr | Met 300 | Glu | Glu 305 | |

-continued

| | | | | | | | | | | | | | | | |
|---|---|---|---|---|---|---|---|---|---|---|---|---|---|---|---|
| CTG | GGG | ATG | CTG | CTG | GGC | GGA | CAG | CCA | ACC | TCC | ACT | CGG | GAG | CAG | ATG | 1078 |
| Leu | Gly | Met | Leu | Leu | Gly | Gly | Gln | Pro | Thr | Ser | Thr | Arg | Glu | Gln | Met |
| | | | 310 | | | | 315 | | | | | | 320 | | |
| CGG | CAG | GTG | CTG | GAG | CTG | GAG | ATA | CAA | CTG | GCC | AAC | ATC | ACG | GTG | CCC | 1126 |
| Arg | Gln | Val | Leu | Glu | Leu | Glu | Ile | Gln | Leu | Ala | Asn | Ile | Thr | Val | Pro |
| | | | 325 | | | | 330 | | | | | | 335 | | |
| CAG | GAC | CAG | CGG | CGG | GAT | GAG | GAG | AAG | ATC | TAC | CAC | AAG | ATG | AGC | ATC | 1174 |
| Gln | Asp | Gln | Arg | Arg | Asp | Glu | Glu | Lys | Ile | Tyr | His | Lys | Met | Ser | Ile |
| | | | 340 | | | | 345 | | | | | | 350 | | |
| GCG | GAG | CTG | CAG | GCC | CTG | GCA | CCC | TCC | ATG | GAT | TGG | CTG | GAG | TTT | CTG | 1222 |
| Ala | Glu | Leu | Gln | Ala | Leu | Ala | Pro | Ser | Met | Asp | Trp | Leu | Glu | Phe | Leu |
| | 355 | | | | | 360 | | | | | 365 | | | | |
| TCC | TTC | TTG | CTG | TCA | CCG | CTG | GAG | CTG | GGT | GAT | TCT | GAG | CCT | GTG | GTG | 1270 |
| Ser | Phe | Leu | Leu | Ser | Pro | Leu | Glu | Leu | Gly | Asp | Ser | Glu | Pro | Val | Val |
| 370 | | | | | 375 | | | | | 380 | | | | | 385 |
| GTG | TAT | GGG | ACG | GAT | TAT | TTG | CAG | CAG | GTG | TCG | GAA | CTC | ATC | AAC | CGC | 1318 |
| Val | Tyr | Gly | Thr | Asp | Tyr | Leu | Gln | Gln | Val | Ser | Glu | Leu | Ile | Asn | Arg |
| | | | | 390 | | | | | 395 | | | | | 400 | |
| ACA | GAG | CCA | AGT | GTC | CTG | AAC | AAT | TAT | CTG | ATC | TGG | AAC | CTG | GTA | CAG | 1366 |
| Thr | Glu | Pro | Ser | Val | Leu | Asn | Asn | Tyr | Leu | Ile | Trp | Asn | Leu | Val | Gln |
| | | | 405 | | | | 410 | | | | | | 415 | | |
| AAG | ACA | ACT | TCA | AGC | CTG | GAC | CAC | CGC | TTT | GAG | TCT | GCA | CAA | GAA | AAG | 1414 |
| Lys | Thr | Thr | Ser | Ser | Leu | Asp | His | Arg | Phe | Glu | Ser | Ala | Gln | Glu | Lys |
| | | | 420 | | | | 425 | | | | | | 430 | | |
| CTG | CTG | GAG | ACC | CTC | TAT | GGC | ACC | AAG | AAG | TCC | TGT | ACA | CCG | AGG | TGG | 1462 |
| Leu | Leu | Glu | Thr | Leu | Tyr | Gly | Thr | Lys | Lys | Ser | Cys | Thr | Pro | Arg | Trp |
| | 435 | | | | | 440 | | | | | 445 | | | | |
| CAG | ACC | TGC | ATC | TCC | AAC | ACC | GAC | GAT | GCT | CTT | GGC | TTT | GCT | CTG | GGC | 1510 |
| Gln | Thr | Cys | Ile | Ser | Asn | Thr | Asp | Asp | Ala | Leu | Gly | Phe | Ala | Leu | Gly |
| 450 | | | | | 455 | | | | | 460 | | | | | 465 |
| TCC | CTC | TTT | GTG | AAG | GCC | ACA | TTT | GAC | CGG | CAG | AGC | AAG | GAA | ATT | GCA | 1558 |
| Ser | Leu | Phe | Val | Lys | Ala | Thr | Phe | Asp | Arg | Gln | Ser | Lys | Glu | Ile | Ala |
| | | | | 470 | | | | | 475 | | | | | 480 | |
| GAG | GGG | ATG | ATC | AGC | GAG | ATC | CGA | GTC | GCC | TTT | GAG | GAG | GCT | CTG | GGA | 1606 |
| Glu | Gly | Met | Ile | Ser | Glu | Ile | Arg | Val | Ala | Phe | Glu | Glu | Ala | Leu | Gly |
| | | | 485 | | | | | 490 | | | | | 495 | | |
| CAC | TTG | GTT | TGG | ATG | GAC | GAG | AAG | ACC | CGC | CAG | GCA | GCC | AAG | GAG | AAA | 1654 |
| His | Leu | Val | Trp | Met | Asp | Glu | Lys | Thr | Arg | Gln | Ala | Ala | Lys | Glu | Lys |
| | | 500 | | | | | 505 | | | | | 510 | | | |
| GCA | GAT | GCC | ATC | TAT | GAT | ATG | ATT | GGT | TTC | CCG | GAC | TTC | ATC | CTG | GAG | 1702 |
| Ala | Asp | Ala | Ile | Tyr | Asp | Met | Ile | Gly | Phe | Pro | Asp | Phe | Ile | Leu | Glu |
| | 515 | | | | | 520 | | | | | 525 | | | | |
| CCC | AAA | GAG | CTG | GAT | GAT | GTT | TAT | GAT | GGG | TAT | GAA | GTA | TCT | GAA | GAT | 1750 |
| Pro | Lys | Glu | Leu | Asp | Asp | Val | Tyr | Asp | Gly | Tyr | Glu | Val | Ser | Glu | Asp |
| 530 | | | | | 535 | | | | | 540 | | | | | 545 |
| TCC | TTC | TTC | CAG | AAC | ATG | TTG | AAT | TTG | TAC | AAC | TTC | TCT | GCT | AAA | GTG | 1798 |
| Ser | Phe | Phe | Gln | Asn | Met | Leu | Asn | Leu | Tyr | Asn | Phe | Ser | Ala | Lys | Val |
| | | | | 550 | | | | | 555 | | | | | 560 | |
| ATG | GCT | GAC | CAG | CTC | CGC | AAG | CCT | CCT | AGC | CGA | GAC | CAG | TGG | AGC | ATG | 1846 |
| Met | Ala | Asp | Gln | Leu | Arg | Lys | Pro | Pro | Ser | Arg | Asp | Gln | Trp | Ser | Met |
| | | | 565 | | | | 570 | | | | | 575 | | | |
| ACC | CCG | CAG | ACA | GTG | AAC | GCC | TAC | TAC | CTT | CCA | ACC | AAG | AAT | GAA | ATC | 1894 |
| Thr | Pro | Gln | Thr | Val | Asn | Ala | Tyr | Tyr | Leu | Pro | Thr | Lys | Asn | Glu | Ile |
| | | 580 | | | | | 585 | | | | | 590 | | | |
| GTC | TTC | CCT | GCT | GGC | ATC | CTG | CAG | GCC | CCC | TTC | TAC | ACT | TGC | AAC | CAC | 1942 |
| Val | Phe | Pro | Ala | Gly | Ile | Leu | Gln | Ala | Pro | Phe | Tyr | Thr | Cys | Asn | His |
| | 595 | | | | | 600 | | | | | 605 | | | | |
| CCC | CAG | GCC | CTG | AAC | TTC | GGT | GGC | ATC | GGT | GTG | GTG | ATG | GGC | CAC | GAG | 1990 |
| Pro | Gln | Ala | Leu | Asn | Phe | Gly | Gly | Ile | Gly | Val | Val | Met | Gly | His | Glu |
| 610 | | | | | 615 | | | | | 620 | | | | | 625 |

```
TTG ACA CAT GCC TTT GAT GAC CAA GGG CGC GAG TAT GAC AAG GAA GGG    2038
Leu Thr His Ala Phe Asp Asp Gln Gly Arg Glu Tyr Asp Lys Glu Gly
            630                 635                 640

AAT CTG CGG CCG TGG TGG CAG AAT GAG TCG TTG GCA GCC TTC CGG AAC    2086
Asn Leu Arg Pro Trp Trp Gln Asn Glu Ser Leu Ala Ala Phe Arg Asn
                645                 650                 655

CAC ACG GCC TGC ATA GAG GAG CAG TAC AGC CAG TAC CAG GTC AAC GGG    2134
His Thr Ala Cys Ile Glu Glu Gln Tyr Ser Gln Tyr Gln Val Asn Gly
        660                 665                 670

GAG AAG CTC AAC GGG CGC CAG ACA CTG GGG GAG AAC ATT GCC GAC AAT    2182
Glu Lys Leu Asn Gly Arg Gln Thr Leu Gly Glu Asn Ile Ala Asp Asn
    675                 680                 685

GGG GGG CTT AAG GCT GCC TAC AAC GCT TAC AAA GCA TGG CTA AGA AAG    2230
Gly Gly Leu Lys Ala Ala Tyr Asn Ala Tyr Lys Ala Trp Leu Arg Lys
690                 695                 700                 705

CAT GGG GAG GAG CAG CAG CTG CCA GCT GTG GGA CTC ACC AAC CAC CAG    2278
His Gly Glu Glu Gln Gln Leu Pro Ala Val Gly Leu Thr Asn His Gln
                710                 715                 720

CTC TTC TTT GTG GGA TTT GCC CAG GTG TGG TGC TCG GTC CGC ACA CCC    2326
Leu Phe Phe Val Gly Phe Ala Gln Val Trp Cys Ser Val Arg Thr Pro
            725                 730                 735

GAG AGC TCT CAC GAG GGG CTG GTG ACC GAC CCC CAC AGC CCT GCC CGC    2374
Glu Ser Ser His Glu Gly Leu Val Thr Asp Pro His Ser Pro Ala Arg
        740                 745                 750

TTC CGT GTG CTG GGC ACT CTC TCC AAC TCC CGT GAC TTC CTG CGG CAC    2422
Phe Arg Val Leu Gly Thr Leu Ser Asn Ser Arg Asp Phe Leu Arg His
    755                 760                 765

TTC GGC TGC CCT GTC GGC TCC CCC ATG AAC TCA GGG CAG CTT TGT GAG    2470
Phe Gly Cys Pro Val Gly Ser Pro Met Asn Ser Gly Gln Leu Cys Glu
770                 775                 780                 785

GTG TGG TAGACCTGGG TTGGGAGAGA AATGGCCAGC TCGGTTGCCG GAGCCTGGGG    2526
Val Trp

TATCTTGCCC AGCCAGGCTC TCTGCTCTGG GGTTGATGGA AGGCACATGC CAGCTGGGCT    2586

GTGTCCTGCC CCTCCACACC ATAGGTGTGA CATGAGTCCT AGTCCTCCT CGGCCTCCAC     2646

ATCGTGCCTC TGCTTTGGGG GTGCCCCTGC CTCCAGCAGA GTCCCCACCA TTCACTGTGA    2706

TGTTCTTTGC CACCCTGCCT GGAGGAGGCC TGGGCAGGGG CCACCAGCTC CCACAAGAAG    2766

GGGTCCACCT CTTTAGGTCC CCAGCTCAGT GGGTTTGGTG GCCACAGGGC CTATTGTGCC    2826

TGCTGACCAC GCAGGGCCCG ACAGATGTGC CTCCCACACA TCTCCCCAAG GCTTACTCAC    2886

TGCTCCCTTG GGCATAGACA GAGCTCCTTT CAGCCCTGCC CCCAGTGGCG ACCTTTATTC    2946

CATGTTCCTC ATGCCACTGC TCCTAATACT GCTGCCAGCC CTCTCTGACG GACCCCCTGT    3006

GCTGAGCTCT TAGTGGAAGT CCAACAGCCT TTACAAACCT TCCTGTTGCC TCCCAGGGTC    3066

CCTGGGCTCA GCGGGGATGT GTGTACATGT CAGGGATGCT AGGCCCTGCA TCTTGGGGTT    3126

ACAAGTCTTA GGGGGTGACT GATTCTCCCT GGACCAAGCA GGAAAGCAGA TAGAGTAGGA    3186

AGAGTGAAGG ATAGAGTCTA TTTTTACAGG AAAGGGTGAG GGGAGGGAGT GGTCTGGCCC    3246

CTGGAGGACC CTGTGCCAAT AAATAGACAC GCATCAGTCA AAAAA                   3291
```

( 2 ) INFORMATION FOR SEQ ID NO:2:

( i ) SEQUENCE CHARACTERISTICS:
        ( A ) LENGTH: 787 amino acids
        ( B ) TYPE: amino acid
        ( D ) TOPOLOGY: linear ( x i ) SEQUENCE DESCRIPTION: SEQ ID NO:2:

Met Arg Ala Arg Tyr Ala His Val Pro Thr Leu Arg Trp Glu Thr Met

```
  1                     5                          10                             15
Asp Val Arg Ala Leu Gly Phe Pro Ser Gly Ser Phe Asp Val Val Leu
            20                      25                  30

Glu Lys Gly Thr Leu Asp Ala Leu Leu Thr Gly Glu Gln Asp Pro Trp
            35                  40                  45

Thr Val Ser Ser Glu Gly Val His Thr Val Asp Gln Val Leu Asn Glu
        50                      55                  60

Ala Gly Phe Arg Lys Arg Thr Ser Arg Leu Leu Gly Leu His Thr Gln
 65                 70                      75                  80

Leu Glu Leu Val Leu Ala Gly Val Ser Leu Leu Ala Ala Leu Leu
                    85                      90                      95

Leu Gly Cys Leu Val Ala Leu Gly Val Gln Tyr His Arg Asp Pro Ser
            100                     105                 110

His Ser Thr Cys Leu Thr Glu Ala Cys Ile Arg Val Ala Gly Lys Ile
            115                     120                 125

Leu Glu Ser Leu Asp Arg Gly Val Ser Pro Cys Glu Asp Phe Tyr Gln
    130                     135                 140

Phe Ser Cys Gly Gly Trp Ile Arg Arg Asn Pro Leu Pro Asp Gly Arg
145                     150                 155                 160

Ser Arg Trp Asn Asn Ser Asn Ser Leu Trp Asp Gln Asn Gln Ala Ile
                165                 170                 175

Leu Lys His Leu Leu Glu Asn Thr Thr Phe Asn Ser Ser Ser Glu Ala
            180                 185                 190

Glu Arg Lys Thr Gln Arg Phe Tyr Leu Ser Cys Leu Gln Val Glu Arg
            195                 200                 205

Ile Glu Glu Leu Gly Ala His Ala Leu Arg Asp Leu Ile Asp Lys Ile
    210                     215                 220

Gly Gly Trp Asn Val Thr Gly Pro Trp Asp Gln Asp Asn Phe Met Glu
225                     230                 235                 240

Val Leu Lys Ala Val Ala Gly Thr Tyr Arg Ala Thr Pro Phe Phe Thr
                245                 250                 255

Val Tyr Val Ser Ala Asp Ser Lys Ser Ser Asn Ser Asn Ile Ile Gln
            260                 265                 270

Val Asp Gln Ser Gly Leu Phe Leu Pro Ser Arg Asp Tyr Tyr Leu Asn
    275                 280                 285

Arg Thr Ala Asn Glu Lys Val Leu Thr Ala Tyr Leu Asp Tyr Met Glu
    290                 295                 300

Glu Leu Gly Met Leu Leu Gly Gly Gln Pro Thr Ser Thr Arg Glu Gln
305                 310                 315                 320

Met Arg Gln Val Leu Glu Leu Glu Ile Gln Leu Ala Asn Ile Thr Val
                325                 330                 335

Pro Gln Asp Gln Arg Arg Asp Glu Glu Lys Ile Tyr His Lys Met Ser
            340                 345                 350

Ile Ala Glu Leu Gln Ala Leu Ala Pro Ser Met Asp Trp Leu Glu Phe
    355                 360                 365

Leu Ser Phe Leu Leu Ser Pro Leu Glu Leu Gly Asp Ser Glu Pro Val
    370                 375                 380

Val Val Tyr Gly Thr Asp Tyr Leu Gln Gln Val Ser Glu Leu Ile Asn
385                 390                 395                 400

Arg Thr Glu Pro Ser Val Leu Asn Asn Tyr Leu Ile Trp Asn Leu Val
            405                 410                 415

Gln Lys Thr Thr Ser Ser Leu Asp His Arg Phe Glu Ser Ala Gln Glu
            420                 425                 430
```

```
Lys Leu Leu Glu Thr Leu Tyr Gly Thr Lys Lys Ser Cys Thr Pro Arg
        435             440             445

Trp Gln Thr Cys Ile Ser Asn Thr Asp Asp Ala Leu Gly Phe Ala Leu
        450             455             460

Gly Ser Leu Phe Val Lys Ala Thr Phe Asp Arg Gln Ser Lys Glu Ile
465             470             475             480

Ala Glu Gly Met Ile Ser Glu Ile Arg Val Ala Phe Glu Glu Ala Leu
                485             490             495

Gly His Leu Val Trp Met Asp Glu Lys Thr Arg Gln Ala Ala Lys Glu
                500             505             510

Lys Ala Asp Ala Ile Tyr Asp Met Ile Gly Phe Pro Asp Phe Ile Leu
            515             520             525

Glu Pro Lys Glu Leu Asp Asp Val Tyr Asp Gly Tyr Glu Val Ser Glu
        530             535             540

Asp Ser Phe Phe Gln Asn Met Leu Asn Leu Tyr Asn Phe Ser Ala Lys
545             550             555             560

Val Met Ala Asp Gln Leu Arg Lys Pro Pro Ser Arg Asp Gln Trp Ser
                565             570             575

Met Thr Pro Gln Thr Val Asn Ala Tyr Tyr Leu Pro Thr Lys Asn Glu
            580             585             590

Ile Val Phe Pro Ala Gly Ile Leu Gln Ala Pro Phe Tyr Thr Cys Asn
            595             600             605

His Pro Gln Ala Leu Asn Phe Gly Gly Ile Gly Val Val Met Gly His
    610             615             620

Glu Leu Thr His Ala Phe Asp Asp Gln Gly Arg Glu Tyr Asp Lys Glu
625             630             635             640

Gly Asn Leu Arg Pro Trp Trp Gln Asn Glu Ser Leu Ala Ala Phe Arg
                645             650             655

Asn His Thr Ala Cys Ile Glu Glu Gln Tyr Ser Gln Tyr Gln Val Asn
            660             665             670

Gly Glu Lys Leu Asn Gly Arg Gln Thr Leu Gly Glu Asn Ile Ala Asp
        675             680             685

Asn Gly Gly Leu Lys Ala Ala Tyr Asn Ala Tyr Lys Ala Trp Leu Arg
    690             695             700

Lys His Gly Glu Glu Gln Gln Leu Pro Ala Val Gly Leu Thr Asn His
705             710             715             720

Gln Leu Phe Phe Val Gly Phe Ala Gln Val Trp Cys Ser Val Arg Thr
                725             730             735

Pro Glu Ser Ser His Glu Gly Leu Val Thr Asp Pro His Ser Pro Ala
            740             745             750

Arg Phe Arg Val Leu Gly Thr Leu Ser Asn Ser Arg Asp Phe Leu Arg
        755             760             765

His Phe Gly Cys Pro Val Gly Ser Pro Met Asn Ser Gly Gln Leu Cys
    770             775             780

Glu Val Trp
785
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Cys  Pro  Val  Gly  Ser  Pro  Met  Asn  Ser  Gln  Leu  Cys  Glu  Val  Trp
 1              5                   10                   15
```

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACAGGGGCTC ACTCCA     16

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTCCAGGATT TTTCCAGCCA CTCGA     25

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGCCTCTGTG AGGCAAGTGC TATG     24

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( x i ) SEQUENCE DESCRIPTION: SEQ ID NO:7:

```
Cys  Pro  Pro  Gly  Ser  Pro  Met  Asn  Pro  His  His  Lys  Cys  Glu  Val  Trp
 1              5                   10                   15
```